US011272832B2

(12) United States Patent
Yamaya

(10) Patent No.: US 11,272,832 B2
(45) Date of Patent: Mar. 15, 2022

(54) COVER REMOVAL JIG FOR ENDOSCOPE, AND ENDOSCOPE SYSTEM

(71) Applicant: Olympus Corporation, Hachioji (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 503 days.

(21) Appl. No.: 16/242,827

(22) Filed: Jan. 8, 2019

(65) Prior Publication Data

US 2019/0142242 A1 May 16, 2019

Related U.S. Application Data

(63) Continuation of application No. PCT/JP2017/025403, filed on Jul. 12, 2017.

(30) Foreign Application Priority Data

Sep. 16, 2016 (JP) .............................. JP2016-181294

(51) Int. Cl.
*A61B 1/00* (2006.01)
*G02B 23/24* (2006.01)

(52) U.S. Cl.
CPC .......... *A61B 1/0014* (2013.01); *A61B 1/0011* (2013.01); *A61B 1/00089* (2013.01); *A61B 1/00098* (2013.01); *A61B 1/00137* (2013.01); *G02B 23/24* (2013.01)

(58) Field of Classification Search
CPC ............ A61B 1/00137; A61B 1/00089; A61B 1/00096; A61B 1/00101
See application file for complete search history.

(56) References Cited

U.S. PATENT DOCUMENTS

| 5,569,157 | A | | 10/1996 | Nakazawa et al. |
| 5,685,823 | A | | 11/1997 | Ito et al. |
| 5,707,344 | A | * | 1/1998 | Nakazawa ............ A61B 1/0008 600/107 |
| 5,730,701 | A | | 3/1998 | Furukawa et al. |
| 10,820,785 | B2 | * | 11/2020 | Yamaya ............. A61B 1/00101 |

(Continued)

FOREIGN PATENT DOCUMENTS

| JP | 06-315458 | 11/1994 |
| JP | 07-184838 | 7/1995 |
| JP | 07-313439 | 12/1995 |

(Continued)

OTHER PUBLICATIONS

International Search Report and Written Opinion from corresponding International Application No. PCT/JP2017/025403, dated Sep. 5, 2017.

Primary Examiner — Matthew J Kasztejna
(74) Attorney, Agent, or Firm — Oliff PLC

(57) ABSTRACT

The disclosed technology is directed to a cover removal jig for an endoscope that removes a tip cover applied to a distal end of an insertion section of an endoscope. The cover removal jig includes an enclosing portion and a cylinder connected to the enclosing portion. The enclosing portion is to be applied to the tip cover to surround its circumference, and has a portion engageable with the tip cover. The cylinder is made from elastic material and capable to come into close contact with a part of an outer surface of the insertion section.

22 Claims, 23 Drawing Sheets

(56) References Cited

U.S. PATENT DOCUMENTS

2003/0088155 A1* 5/2003 Ishibiki .................. A61B 1/042
600/127

FOREIGN PATENT DOCUMENTS

| JP | 08-187219 | 7/1996 |
| JP | 09-075295 | 3/1997 |
| JP | 10-127578 | 5/1998 |
| JP | 2004-229987 | 8/2004 |
| JP | 2004-298442 | 10/2004 |

* cited by examiner

COVER REMOVAL JIG FOR ENDOSCOPE, AND ENDOSCOPE SYSTEM

CROSS-REFERENCE TO RELATED APPLICATIONS

This application is a continuation application of PCT Application No. PCT/JP2017/025403 filed on Jul. 12, 2017, which in turn claim priority to the Japanese Patent Application No. 2016-181294 filed on Sep. 16, 2016 in Japan which is hereby incorporated by reference in its entirety.

TECHNICAL FIELD

This technology disclosed herein generally relates to a cover removal jig for an endoscope, which is useful in removing a tip cover, and also to an endoscope system.

DESCRIPTION OF THE RELATED ART

In JP 1994-315458A, for example, an endoscope having a forceps elevator pivotally disposed on a distal end portion of an insertion portion is disclosed. This endoscope has a tip cover that surrounds the distal end portion of the insertion portion, the forceps elevator that sets a direction in which forceps delivered from the distal end portion of the insertion portion are to extend, and an operation wire that causes the forceps elevator to pivot. The tip cover, forceps elevator and operation wire can be detached from a main body of the endoscope upon cleaning.

BRIEF SUMMARY OF EMBODIMENTS

After use of the endoscope and before cleaning of the same, the tip cover, forceps elevator and operation wire are detached from the main body of the endoscope. Here, the tip cover may be stained with body fluids and the like of a subject under examination or surgery, so that upon detachment of the tip cover, a slip may occur and the detachment work may not proceed with ease.

This disclosure has as an object thereof the provision of a cover removal jig for an endoscope, which has improved workability upon removal of the tip cover.

A cover removal jig according to an aspect of the present disclosure for an endoscope is a cover removal jig for removing a first tip cover applied to a distal end of an insertion portion of the endoscope; and includes a first enclosing portion to be applied to the first tip cover to surround a circumference of the first tip cover and having a portion engageable with the first tip cover, and a cylinder connected to the first enclosing portion, capable of coming into close contact with a part of an outer surface of the insertion portion, and having elasticity.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

An embodiment for carrying out this disclosure will hereinafter be described with reference to the drawings.

Figure 1:
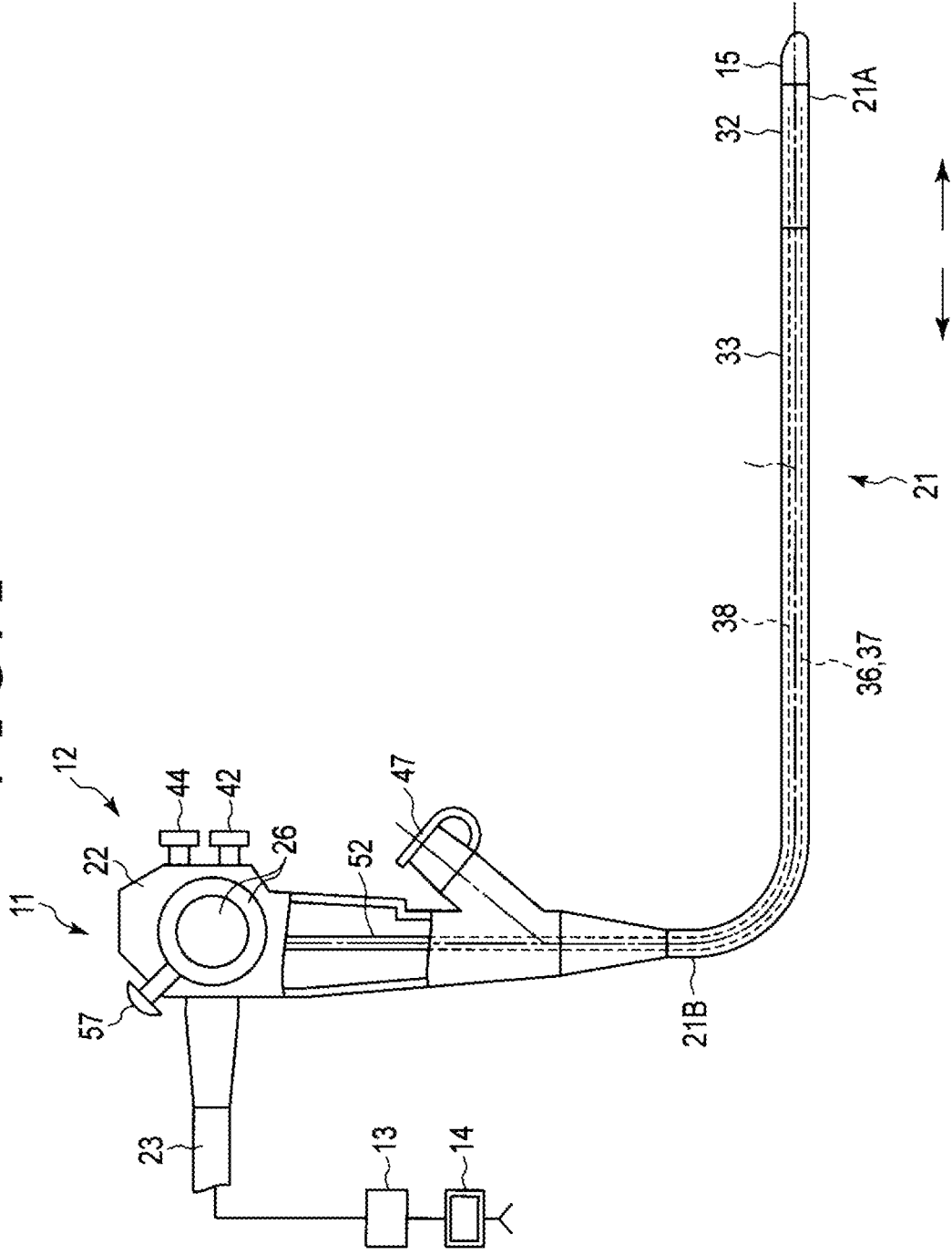
FIG. 1 is a schematic view of an endoscope system according to an embodiment.

Referring to FIGS. 1 through 16, a description will be made about an endoscope system according to an embodiment. As illustrated in FIGS. 1 and 7, the endoscope system 11 includes an endoscope 12, an endoscope controller 13 or image processing unit that performs image processing based on images of a subject as captured by the endoscope 12, a monitor 14 that displays a video image created by the image processing at the endoscope controller 13, and a cover removal jig 16 for removing a tip cover 15 from the endoscope 12.

Figure 2:
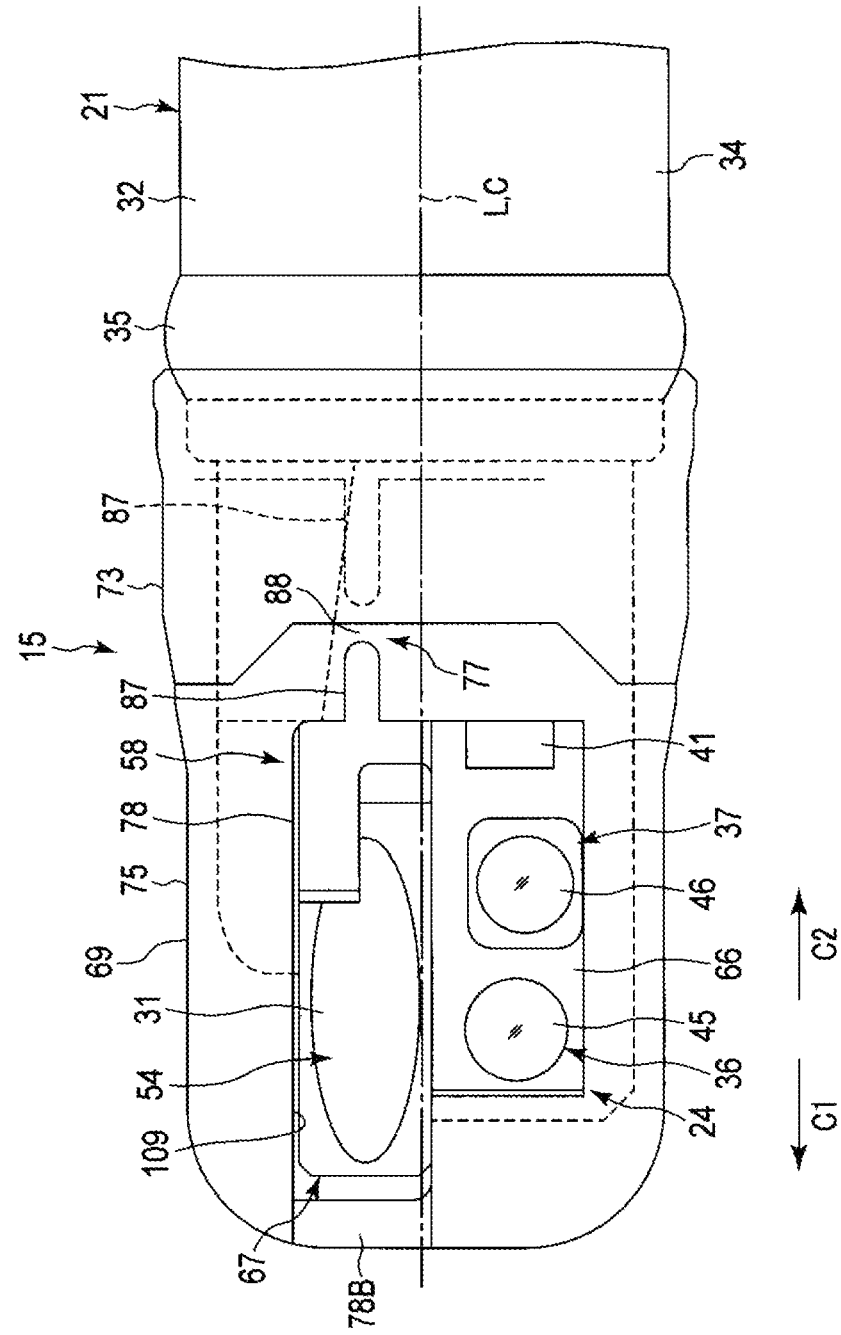
FIG. 2 is a schematic plan view illustrating a distal end structure part in the endoscope system illustrated in FIG. 1 and a tip cover applied to the distal end structure part.

As illustrated in FIGS. 1 and 2, the endoscope 12 has an insertion portion 21 that is inserted along a longitudinal direction L in a biological channel such as a lumen of a subject under examination or surgery, the tip cover 15, cover or sheath that is applied to a distal end of the insertion portion 21, a control section 22 that is disposed on a proximal end of the insertion portion 21 and is gripped by an operator, a universal cord 23 that extends from the control section 22, and a distal end structure part 24 that is disposed on the side of the distal end of the insertion portion 21 and is rigid. Although details will be described later, the tip cover 15 is formed as a disposable type, and is also formed so that it can be easily applied to the distal end structure part 24 of the insertion portion 21 while retaining its shape but cannot be easily detached from the distal end structure part 24 owing to an engagement pin 65 to be described subsequently herein or the like.

As illustrated in FIG. 1, the insertion portion 21 defines the longitudinal direction L by its distal end 21A and proximal end 21B. As illustrated in FIGS. 1 and 2, the insertion portion 21 has a rockable base 31, the distal end structure part 24, a bending section 32 and a tube part 33 in this order from the distal end 21A toward the proximal end 21B. The tube part 33 may be one so-called "soft endoscope" and having flexibility, or may be one so-called "rigid endoscope" and having durability against bending while maintaining a straight form. By a known mechanism, the bending section 32 can be bent in plural directions such as two directions or four directions by a knob 26 in the control section 22. The insertion portion 21 includes a sheath 34 that makes up an outer shell of the bending section 32 and has elasticity, and a wound thread coil 35 that is formed with a thread wound on and around an outer circumference of the sheath 34 to fix the sheath 34 on the distal end structure part 24. The wound thread coil 35 is covered at a surface thereof with a resin layer. It is to be noted that in this embodiment, the description will hereinafter proceed by representing, as "C1," a direction toward the distal end of the insertion portion 21 as viewed in the longitudinal direction L and representing, as "C2," a direction toward the proximal end as viewed in the longitudinal direction L, that is, a direction toward the distal end. The distal end structure part 24 is disposed on the distal end of the insertion portion 21. The distal end structure part 24 has a central axis C as will be described subsequently herein, and this central axis C is coincided with the longitudinal direction L.

As illustrated in FIG. 1, the endoscope 12 has an illumination optical system 36, an observation optical system 37, and an instrument insertion channel 38. In addition, the endoscope 12 also has an air supply/water supply mechanism and a suction mechanism although they are not illustrated in the drawing. The air supply/water supply mechanism has a below-described nozzle 41 at a distal end thereof, and is operated by a first button 42 in the control section 22. The suction mechanism is in communication with the instrument insertion channel 38, and is operated by a second button 44 in the control section 22.

The illumination optical system 36 and observation optical system 37 are inserted through the distal end structure part 24, bending section 32 and tube part 33 of the insertion portion 21, the control section 22, and the universal cord 23 of the endoscope 12. As illustrated in FIG. 2, the illumination optical system 36 has a lighting window 45 in the distal end structure part 24. The observation optical system 37 has an observation window 46 in the distal end structure part 24.

Figure 12:
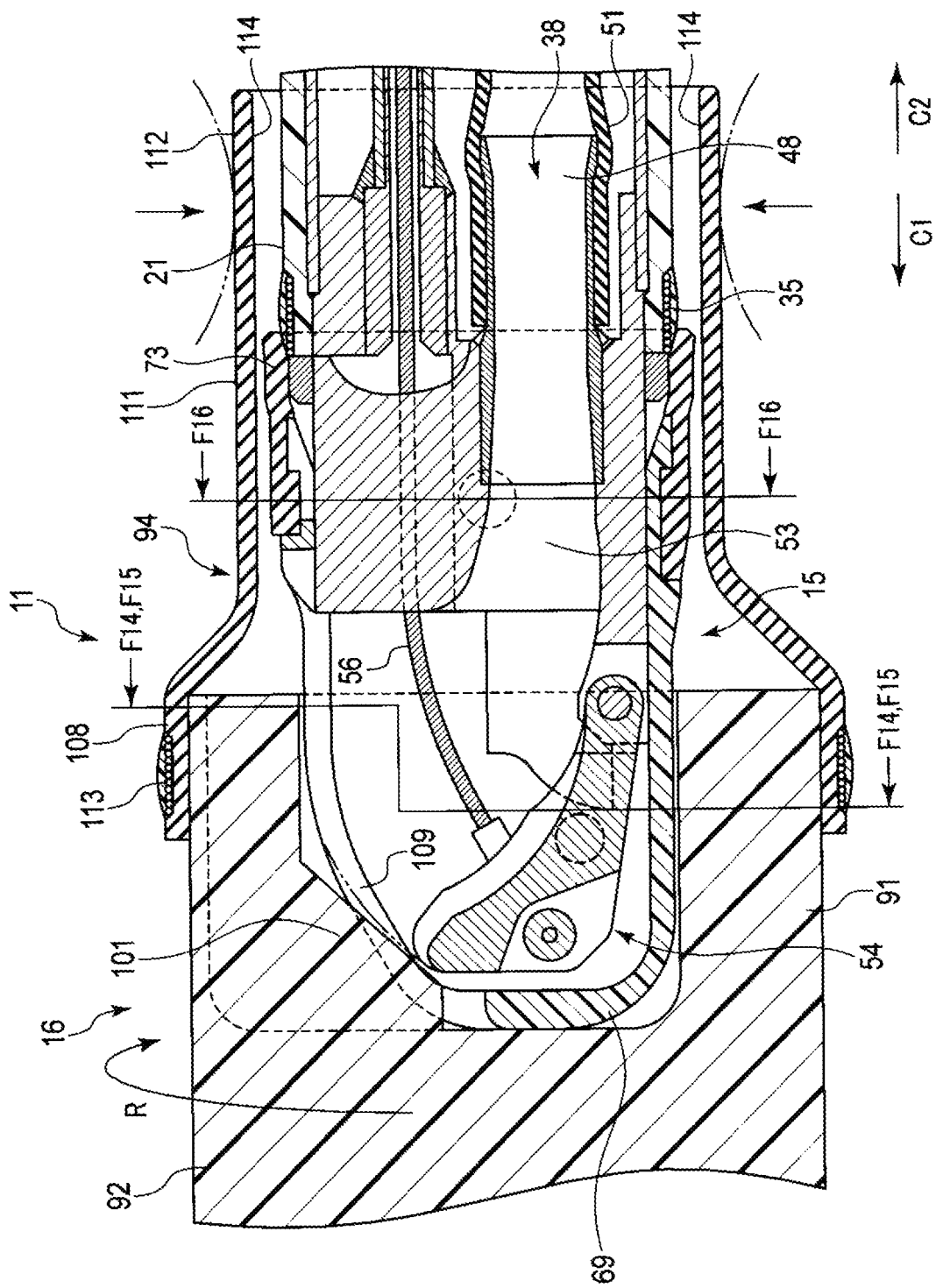
FIG. 12 is a cross-sectional view illustrating the distal end structure part, tip cover and cover removal jig of FIG. 11 as taken on a plane along a central axis.

The instrument insertion channel 38 opens at a distal end thereof in the distal end structure part 24 of the insertion portion 21 of the endoscope 12, and opens at a proximal end thereof in the vicinity of a proximal end portion of the tube part 33 of the insertion portion 21 or in the control section 22. In this embodiment, the control section 22 includes an opening (not depicted) of a proximal end of the instrument insertion channel 38, and as illustrated in FIG. 1, a biopsy valve 47 is detachably fitted in the opening with a tip reinforcement member interposed therebetween. As illustrated in FIG. 12, the instrument insertion channel 38 is formed by a tube 51, which is fixedly secured to the distal end structure part 24 with a tip reinforcement member 48 interposed therebetween. It is to be noted that the tube 51 of the instrument insertion channel 38 branches into a known suction line 52, for example, inside the control section 22. The suction line 52 is connected to the second button 44. By pressing operation of the second button 44, aspirate is discharged from a below-described opening 53 at the distal end of the instrument insertion channel 38 via the tip reinforcement member 48, tube 51, suction line 52 and universal cord 23.

In this embodiment, the endoscope 12 is formed as a side view type having an observation direction different from a direction along the longitudinal direction L of the insertion portion 21. As illustrated in FIG. 2, the endoscope 12 has a rocking mechanism 54 that adjusts the direction of a surgical instrument (not depicted), which has been inserted through the instrument insertion channel 38, as desired by the distal end structure part 24 and enables to observe the surgical instrument in a visual field.

Figure 4:
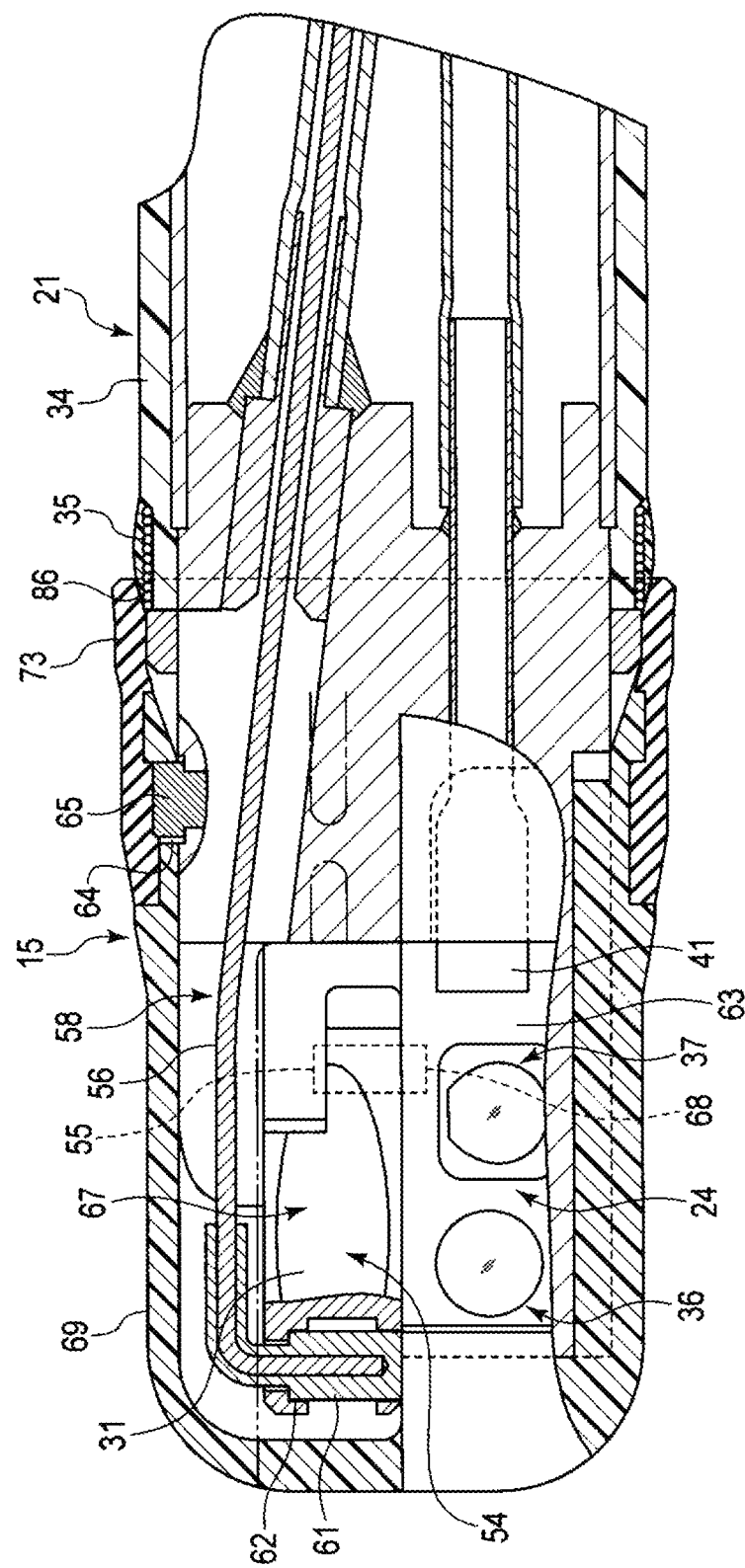
FIG. 4 is a cross-sectional view illustrating the distal end structure part and the tip cover applied to the distal end structure part, which are illustrated in FIG. 2, as taken on a plane along a longitudinal direction.

As illustrated in FIG. 4, the rocking mechanism 54 has the rockable base 31 or a pivotal portion, surgical instrument elevator or elevator, a rotatable shaft 55 disposed integrally with the rockable base 31, a wire 56 or pull member extending linearly, and a lever 57 (see FIG. 1) in this order from the distal end toward the proximal end of the insertion portion 21. The rockable base 31 is supported on the distal end structure part 24 via the rotatable shaft 55, and can rock or raise the surgical instrument at the distal end of the insertion portion 21. The wire 56 is supported at a distal end thereof on the rockable base 31, and is supported at a proximal end thereof on the lever 57. The wire 56 is connected to the rockable base 31 in a wire moving area 58 located in the distal end structure part 24, and can perform remote operation of the rockable base 31. The wire 56 includes at the distal end thereof an operating shaft portion 61 formed in an "L" letter shape. The operating shaft portion 61 is fitted in a receiving portion 62 of the rockable base 31 so that the operating shaft portion 61 is rotatable relative to the receiving portion 62 and does not come off from the receiving portion 62. The rockable base 31 is a surgical instrument elevator that elevates or raises the surgical instrument, which has been inserted along the insertion portion 21 into the subject under examination or surgery, relative to the insertion portion 21.

Figure 5:
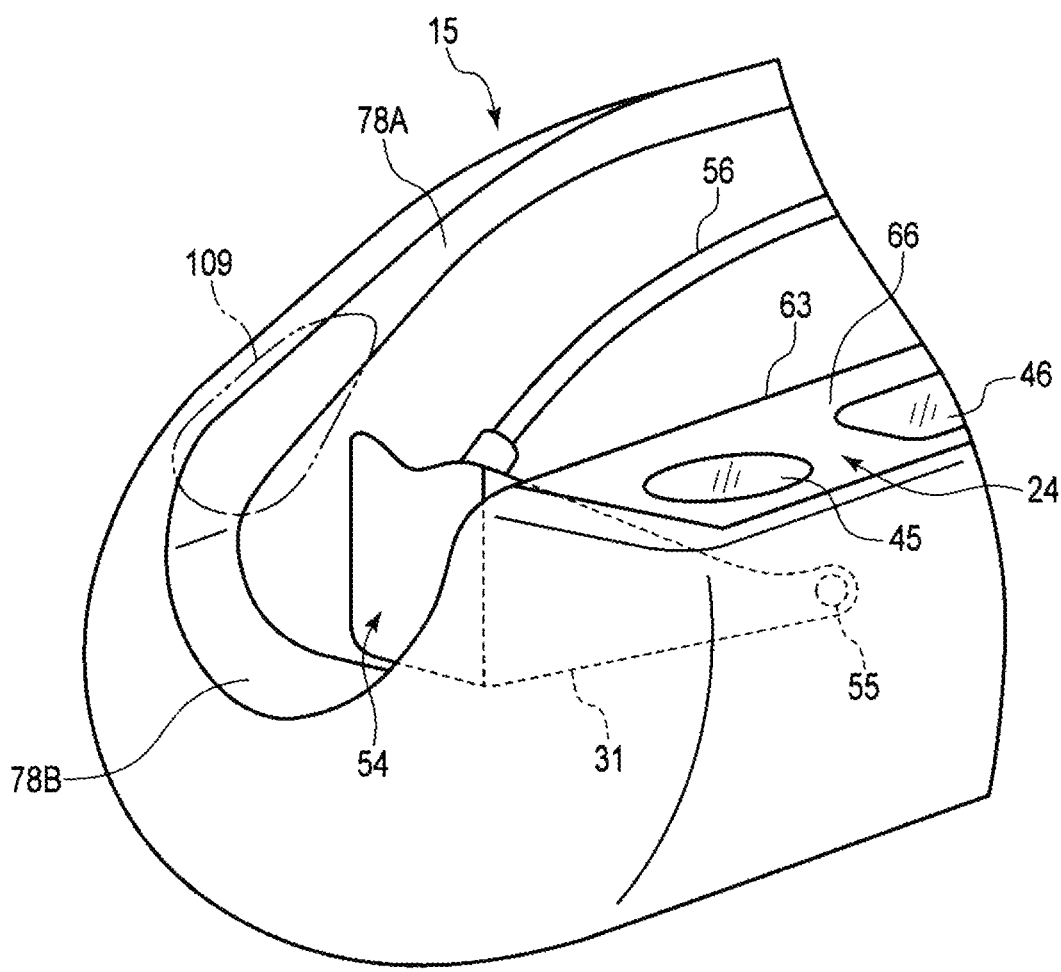
FIG. 5 is an enlarged fragmentary perspective view of the distal end structure part and tip cover illustrated in FIG. 2.
Figure 6:
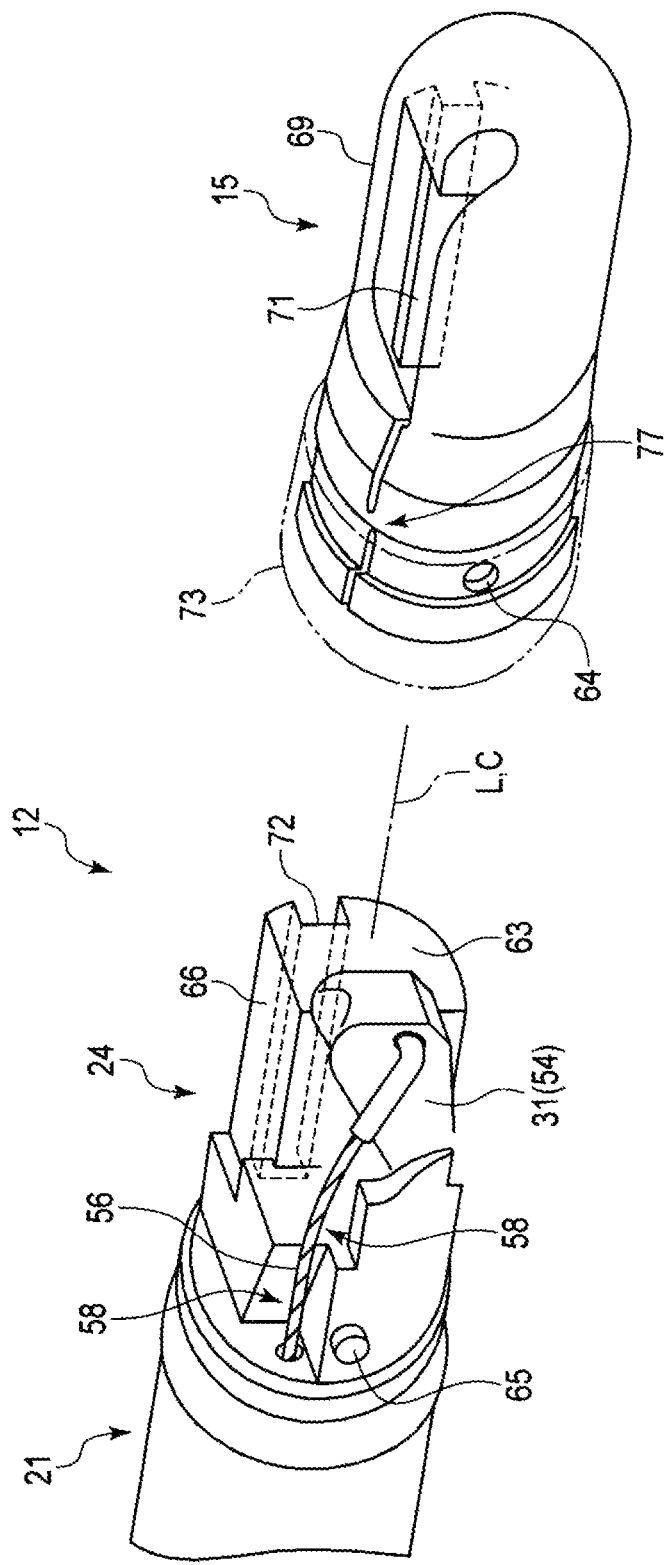
FIG. 6 is a perspective view illustrating a state before attachment of the tip cover to the distal end structure part as illustrated in FIG. 2.
Figure 7:
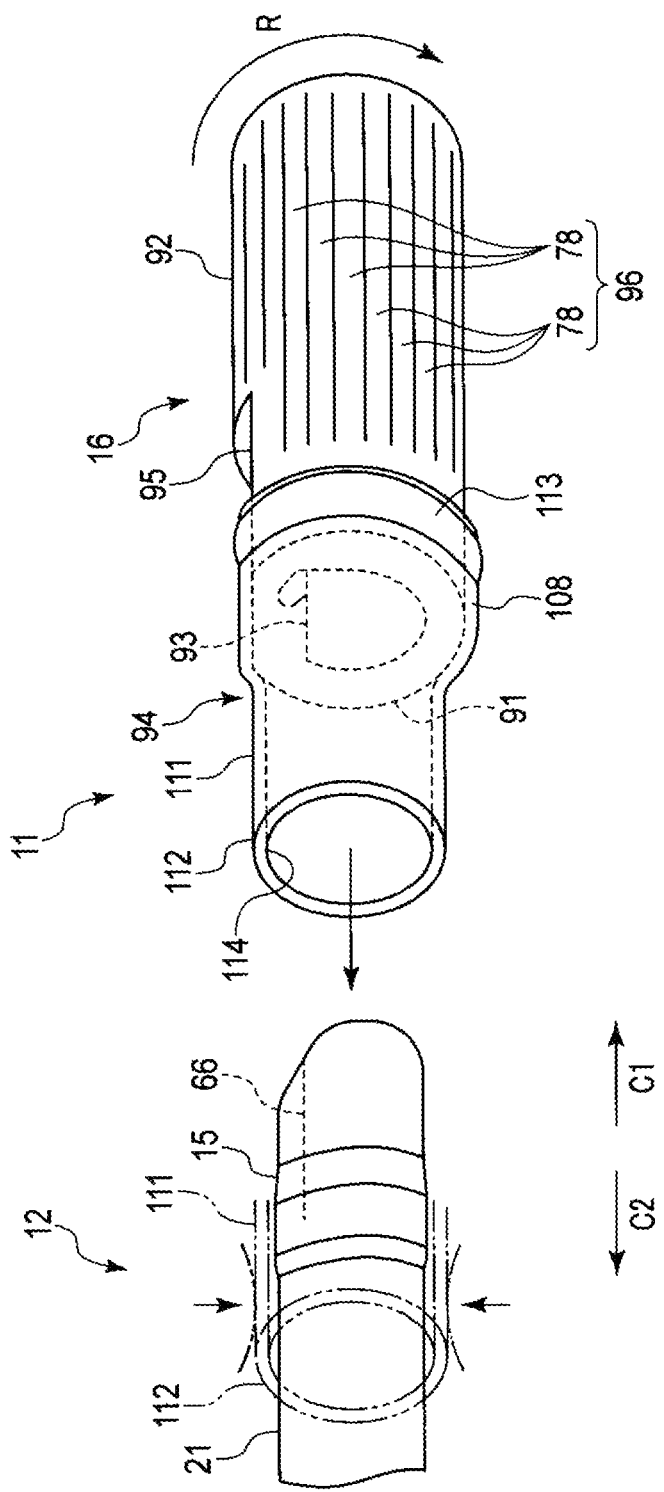
FIG. 7 is a perspective view illustrating a cover removal jig in the endoscope system according to the embodiment.

As illustrated in FIG. 6, etc., the distal end structure part 24 has a block-shaped main body 63, and the engagement pin 65 that is disposed projecting from the main body 63 and is engageable with an engagement hole 64 of the tip cover 15. The main body 63 is formed of a metal material such as stainless steel. As illustrated in FIGS. 5 and 12, the main body 63 includes the lighting window 45 at the distal end of the illumination optical system 36, the observation window 46 at the distal end of the observation optical system 37, and the opening 53 connected to a distal end portion of the tube 51 of the instrument insertion channel 38. The rockable base 31 at a distal end portion of the rocking mechanism 54 is pivotally attached to the main body 63. The opening 53 is in communication with a below-described accommodation space 67 and also with the instrument insertion channel 38, and guides the surgical instrument to the rockable base 31.

As illustrated in FIGS. 4 to 6, the main body 63 has a planar portion 66 with the lighting window 45 and observation window 46 fixed therein, the accommodation space 67 with the rockable base 31 rockably accommodated therein, the wire moving area 58 or a wire moving space formed in continuation with the accommodation space 67, bearings 68 with the rotatable shaft 55 of the rockable base 31 pivotally held thereon, and a guide groove 72 into which a guide protrusion 71 of a cover main body 69 is inserted.

The planar portion 66 of the main body 63 is parallel to the longitudinal direction L. The nozzle 41 is disposed on the side of a proximal end of the observation window 46. The nozzle 41 is directed toward the observation window 46 and lighting window 45. The nozzle 41 can squirt liquid such as physiological saline toward the observation window 46 and lighting window 45, and can also supply air to blow off deposits from the observation window 46 and lighting window 45.

As illustrated in FIG. 6, the guide groove 72 is disposed recessed from an outer circumferential wall of the main body 63. The guide groove 72 is disposed adjacent the planar portion 66 and along the longitudinal direction L. The guide groove 72 is formed continuously from the side of a distal end to the side of a proximal end of the main body 63. The engagement pin 65 projects in a direction orthogonal to the central axis C. The engagement pin 65 is formed in a columnar shape.

Figure 3:
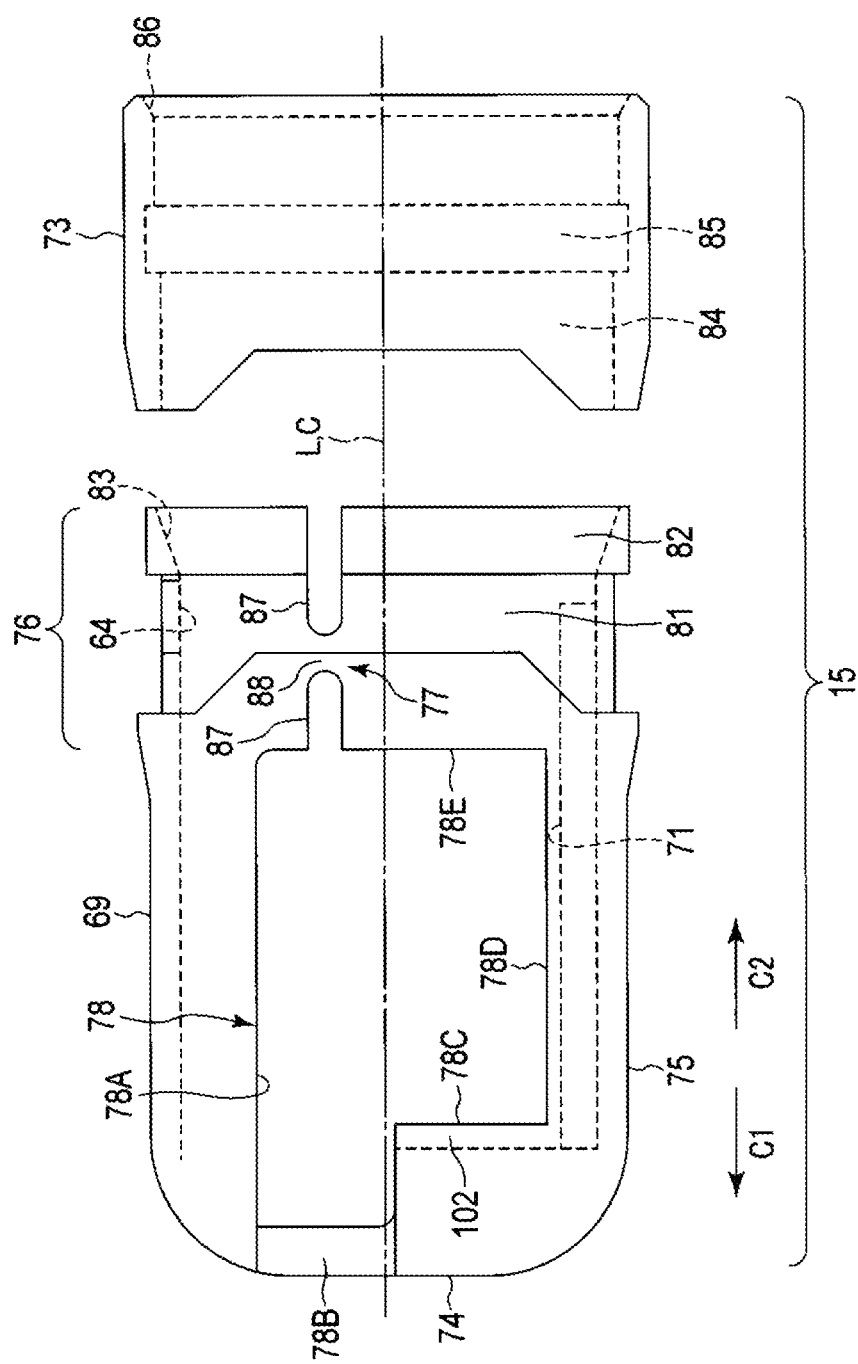
FIG. 3 is a plan view illustrating, in an exploded view, a cover main body and a holding ring in the tip cover illustrated in FIG. 2.

As illustrated in FIGS. 2 and 3, the tip cover 15 has the cover main body 69 and a holding ring 73. The cover main body 69 is formed, for example, in a bottomed cylindrical shape. The cover main body 69 is formed, for example, of a general resin material or plastics such as polysulfone, polyethylene or polycarbonate.

The holding ring 73 is formed in a cylindrical or annular shape, for example, with a material having rubber elasticity, in other words, a rubber material. The holding ring 73 is formed, for example, with silicone rubber, fluororubber or the like. It is to be noted that the cover main body 69 and holding ring 73 may preferably be formed of a material having electrical insulating property. The cover main body 69 and holding ring 73 each have an inner diameter or an inner circumferential wall, which is determined to have an appropriate size and shape based on the size and shape of the distal end structure part 24.

The cover main body 69 has a closed portion 74 disposed at a distal end thereof, a rotating circumferential wall 75 disposed on an outer circumference thereof, an annular part 76 disposed at a proximal end thereof, and a weakened portion 77 disposed at the annular part 76. The closed portion 74 is formed in a substantially hemi-spherical shape. A proximal end of the cover main body 69, in other words, the annular part 76 is open. The cover main body 69 has a substantially rectangular opening edge portion 78 or opening portion between the closed portion 74 and the annular part 76. The opening edge portion 78 externally exposes the lighting window 45, observation window 46, nozzle 41 and rockable base 31 in the distal end structure part 24.

As illustrated in FIG. 3, the opening edge portion 78 has a right-side edge portion 78A extending along the longitudinal direction L and located on a right side, a U-shaped indented edge portion 78B continuing from the right-side edge portion 78A, a distal end-side edge portion 78C continuing from the indented edge portion 78B, a left-side edge portion 78D continuing from the distal end-side edge portion 78C, extending along the longitudinal direction L and located on a left side, and a proximal end-side edge portion 78E located between proximal ends of the right-side edge portion 78A and left-side edge portion 78D. With these right-side edge portion 78A, indented edge portion 78B, distal end-side edge portion 78C, left-side edge portion 78D and proximal end-side edge portion 78E, the opening edge portion 78 forms a closed ring. The right-side edge portion 78A and the left-side edge portion 78D may preferably be parallel or substantially parallel to each other. The distal end-side edge portion 78C and the proximal end-side edge portion 78E may preferably be parallel or substantially parallel to each other. Without being limited to a time that the rockable base 31 causes the surgical instrument to rock, the endoscope 12 always exposes the rockable base 31 through the opening edge portion 78 or opening portion (see FIG. 5).

As illustrated in FIG. 3, the annular part 76 has, on an outer circumferential wall thereof, a fitting portion 81 and a flange portion 82, with which the holding ring 73 is fitted. The annular part 76 is formed, at an inner circumference thereof, into a tapered portion 83 that becomes progressively thinner in the direction C2 toward the proximal end along the longitudinal direction L. The tapered portion 83 has an inner diameter that becomes progressively greater in the direction C2 toward the proximal end.

As illustrated in FIGS. 2 and 3, the holding ring 73 has, on an inner circumferential wall thereof, an annular convex portion 84 to be fitted in the fitting portion 81 and an annular engagement concave portion 85 to be fitted on the flange portion 82. Therefore, as illustrated in FIG. 2, the holding ring 73 can be brought into fitting engagement with the annular part 76 of the cover main body 69. The holding ring 73 has a second tapered portion on an inner circumferential wall thereof. As illustrated in FIG. 4, the wound thread coil 35 or a fixing portion on the side of the insertion portion 21 fits in the second tapered portion 86 and is kept in water-tight close contact with the second tapered portion 86. The second tapered portion 86 becomes progressively thinner toward the side of the proximal end along the longitudinal direction L, and has an inner diameter that progressively increases in the direction C2 toward the proximal end.

As illustrated in FIGS. 3 and 4, the engagement hole 64 or engagement portion, in which the engagement pin 65 fits or with which the engagement pin 65 engages, is formed through the annular part 76 of the cover main body 69. The engagement hole 64 is formed as a through-hole, but may also be formed simply in a concave shape on the inner circumferential wall of the cover main body 69. The engagement hole 64 may suitably be formed through the fitting portion 81.

As illustrated in FIGS. 3 and 4, the guide protrusion 71 is formed on the inner circumferential wall of the cover main body 69. As illustrated in FIG. 6, the guide protrusion 71 is formed movably along the guide groove 72, and extends inwardly in a radial direction from the inner circumferential wall of the cover main body 69. The guide protrusion 71 is formed in a substantially rectangular shape in cross-section so that the guide protrusion 71 conforms in shape to the guide groove 72.

As illustrated in FIGS. 2 and 3, the weakened portion 77 has a pair of slits 87, 87 and a connecting portion 88 or break-off portion located between the slits 87, 87. One of the slits 87, 87 is formed in continuation with the proximal end-side edge portion 78E. The other slit 87 is formed in continuation with the flange portion 82. In this embodiment, the slits 87, 87 are both formed along the longitudinal direction L. It is to be noted that the engagement hole 64 is formed at a position turned by approximately 90° about the central axis C with respect to the connecting portion 88. On the other hand, the guide protrusion 71 is formed at a position located on a side opposite to the engagement hole 64 and turned in a circumferential direction by approximately 90° about the central axis C with respect to the connecting portion 88. As illustrated in FIG. 6, the weakened portion 77 may preferably be disposed over the wire moving area 58 of the main body 63 of the distal end structure part 24. The weakened portion 77 is broken upon removal of the tip cover 15 from the distal end structure part 24.

As illustrated in FIGS. 2 and 3, the rotating circumferential wall 75 is formed as a part of a cylinder. The central axis C of the tip cover 15 and distal end structure part 24 is defined by the rotating circumferential wall 75. This rotating circumferential wall 75 fits inside a below-described enclosing portion 91 of the cover removal jig 16.

Upon application of the tip cover 15 to the distal end structure part 24, the holding ring 73 is applied to the cover main body 69 beforehand so that they are integrated together as depicted in FIG. 6. The tip cover 15 integrated as described above is then applied to the distal end structure part 24. The engagement pin 65 is fitted in the engagement hole 64 while allowing the cover main body 69 to undergo an elastic deformation at a part thereof, whereby the tip cover 15 can be readily applied to the distal end structure part 24. Nonetheless, the tip cover 15 has been applied such that it cannot be easily removed from the distal end structure part 24 without breaking the weakened portion 77.

The endoscope 12 is inserted at the insertion portion 21 thereof into a biological channel such as a lumen with the tip cover 15 being applied to the distal end structure part 24, and observation and desired treatment are performed. It is to be noted that the weakened portion 77 is covered and protected by the holding ring 73. The weakened portion 77 is, therefore, suppressed from being broken off even if it comes into contact, for example, with the inner wall or the like of a biological passage such as a lumen during insertion into such a biological channel or during treatment.

Figure 8:
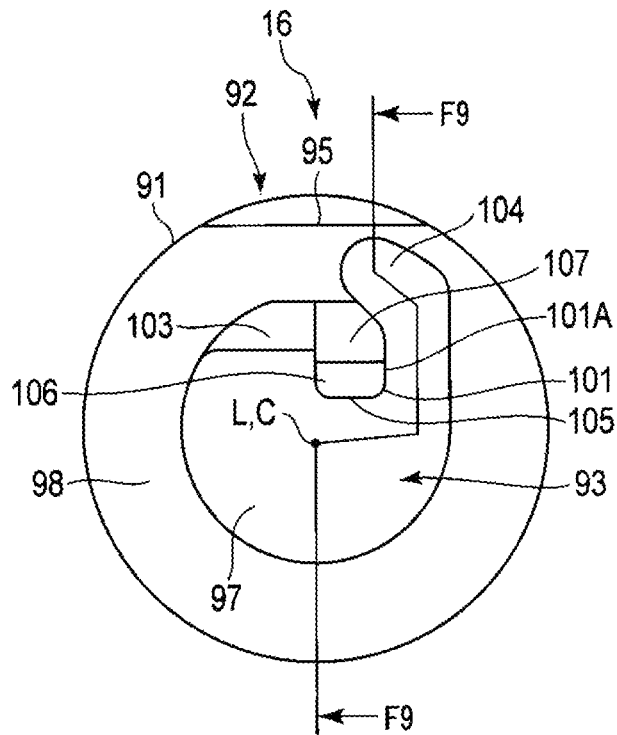
FIG. 8 is a front view of the cover removal jig of FIG. 7, with a cylinder having been detached, as viewed from a front.
Figure 9:
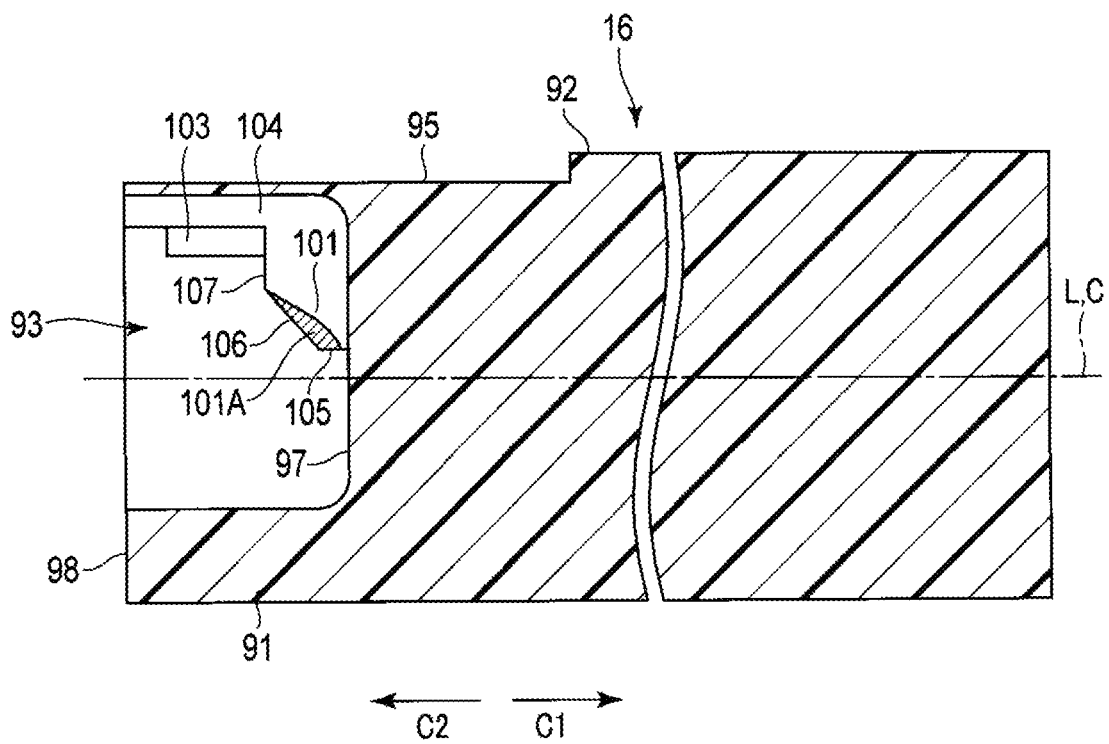
FIG. 9 is a cross-sectional view of the cover removal jig of FIG. 8 as taken along a position of line F9-F9.
Figure 10:
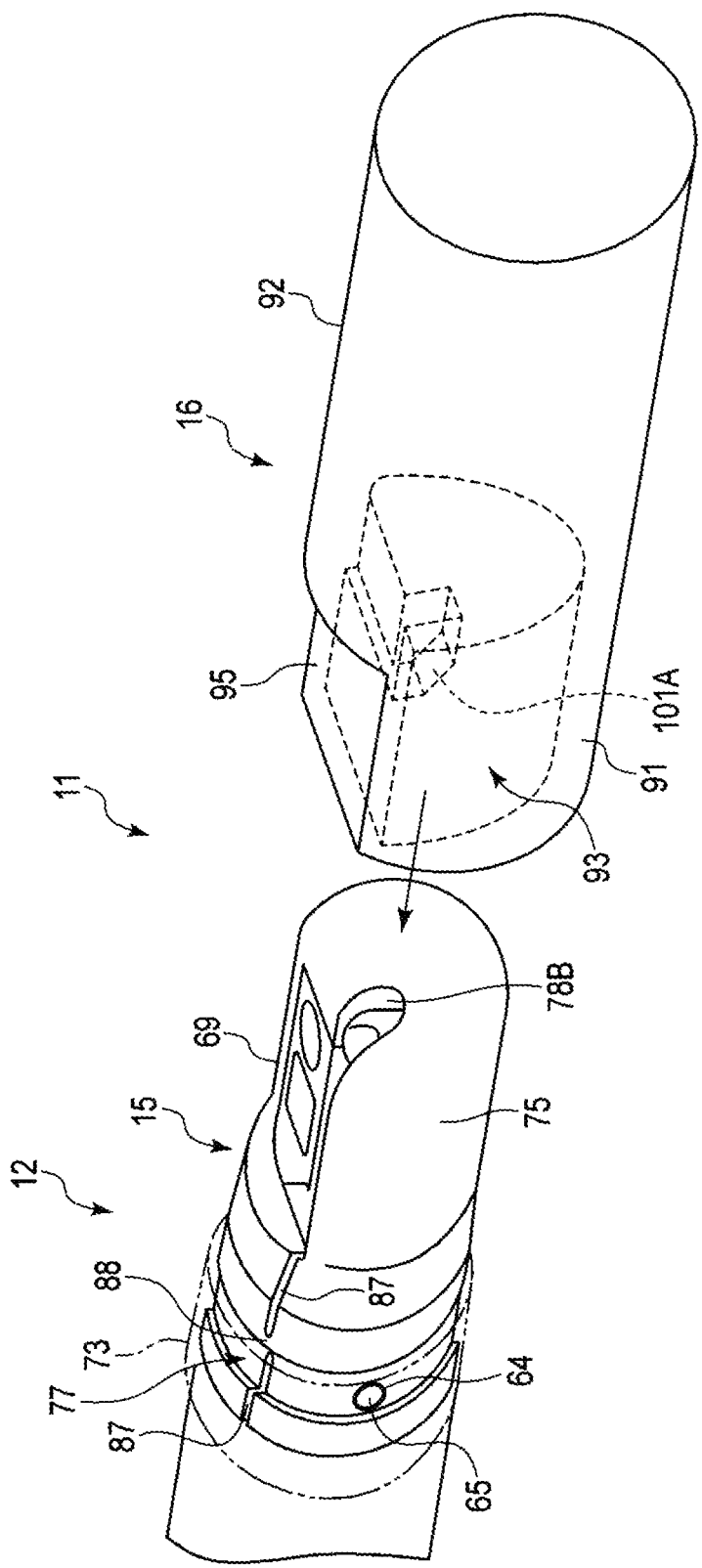
FIG. 10 is a perspective view illustrating, with omission of the cylinder, a step of applying the cover removal jig to the distal end structure part and tip cover of FIG. 2.

With reference to FIGS. 7 to 9, a description will hereinafter be made about the cover removal jig 16. The cover removal jig 16 is formed of a resin material harder than the cover main body 69 of the tip cover 15, for example, fiber reinforced plastics such as glass fiber reinforced plastics, or a metal material. More specifically, the cover removal jig 16 is formed of modified PPE resin, glass-filled polysulfone, polyphenylsulfone, stainless steel, or the like.

On the other hand, the distal end structure part 24 is formed of a general metal material, for example, stainless steel or the like. Described specifically, the cover removal jig 16 includes a working portion 93, which is formed of a material harder than the tip cover 15 but softer than the distal end structure part 24. As a consequence, the weakened portion 77 of the tip cover 15 can be easily broken while avoiding careless damage to the distal end structure part 24.

As illustrated in FIG. 7, the cover removal jig 16 has a columnar grip handle 92 grippable by an operator, the working portion 93 disposed on an end portion of the grip handle 92, a cylinder 94 having elasticity and flexibly connected to a below-described enclosing portion 91 of the working portion 93, and a marker 95 arranged on the grip handle 92 and working portion 93. On an outer circumferential wall of the grip handle 92, a plurality of flutes 78 are formed extending in the direction of the central axis C. Each flute 78 may preferably have, for example, an arcuate cross-sectional shape. The flutes 78 make up an anti-slip portion, or third anti-slip portion 96, as a slip resistant element for the operator's hand. The grip handle 92 has an outer diameter greater than the insertion portion 21.

The marker 95 is formed as a planar surface on the outer circumferential wall of the grip handle 92 and an outer circumferential wall of the working portion 93 or enclosing portion 91. By touching the marker 95, the operator can perceive an angle of the cover removal jig 16 about the central axis C in the circumferential direction. As readily appreciated from the foregoing, the external form of the cover removal jig 16 is not limited specifically.

As illustrated in FIGS. 8 and 9, the working portion 93 has a bottom portion 97 that is brought into contact with the distal end of the tip cover 15, the cylindrical enclosing portion 91 that extends from the bottom portion 97 and can cover a circumference of the tip cover 15, an end face 98 disposed at a distal end of the enclosing portion 91, a first protrusion 101 that is fitted in the U-shaped indented edge portion 78B at the opening edge portion 78 of the tip cover 15 or an opening portion of the tip cover 15, a second protrusion 103 that is fitted on a distal end-side cover portion 102 of the cover main body 69 and is flush with the planar portion 66 of the distal end structure part 24, and a receiving recess 104 in which a portion of the right-side edge portion 78A of the opening edge portion 78 of the broken tip cover 15 is placed. The first protrusion 101 or a protrusion has a stepped portion 105 that extends in the direction of the central axis C, an inclined portion 106 that is inclined away from the central axis C progressively in the direction C2 toward the proximal end, and a top wall portion 107 that is disposed on a side in the direction C2 toward the proximal end. The first protrusion 101 which is a portion to engage the tip cover is integrally formed with the enclosing portion 91, and in other words, is disposed as a portion of the enclosing portion 91. Further, the grip handle 92 is disposed in continuation with the enclosing portion 91 on a side opposite to the side where the cylinder 94 is connected.

The enclosing portion 91 has an inner diameter formed slightly greater than the diameter of the tip cover 15 as defined by the rotating circumferential wall 75. The first protrusion 101 has a width formed slightly smaller than the width of the indented edge portion 78B of the tip cover 15. As illustrated in FIG. 9, the first protrusion 101 of the cover removal jig 16 has a pressing portion 101A. The pressing portion 101A is brought into contact with a pressed portion 109 (see FIG. 5) between the indented edge portion 78B and the right-side edge portion 78A of the opening edge portion 78 in the tip cover 15.

As illustrated in FIGS. 7 and 12, the cylinder 94 has a cylindrical shape as a whole. The cylinder 94 has a sleeve portion 108 connected to the enclosing portion 91, a reduced diameter portion 111 having a diameter smaller than the sleeve portion 108 on a side in the direction C2 toward the proximal end, specifically on a side opposite to the sleeve portion 108, and a distal end portion 112 disposed at an end portion of the reduced diameter portion 111 and located on a side opposite to the sleeve portion 108. The distal end portion 112 and reduced diameter portion 111 cover the tip cover 15, the wound thread coil 35, and a part of the insertion portion 21. The cylinder 94 has an inner diameter formed slightly greater than an outer diameter of the holding ring 73 of the tip cover 15. A slight clearance is, therefore, left between the holding ring 73 and the cylinder 94 in a state that the insertion portion 21 is covered by the cylinder 94 (see FIG. 12).

The cylinder 94 is formed as a unitary member from a material having rubber elasticity. The cylinder 94 may be formed, for example, of silicone rubber, fluororubber, urethane rubber, soft urethane resin, acrylic elastomer, soft PVC, polyvinyl chloride, or the like. The sleeve portion 108 of the cylinder 94 is firmly fixed by a second wound thread coil 113 formed with a thread wound on and around an outer circumference of the cylinder 94, so that the sleeve portion 108 is integrated with the enclosing portion 91. The second wound thread coil 113 is covered at a surface thereof with a resin. On an inner circumferential wall of the cylinder 94, an anti-slip portion 114 is formed as a slip resistant element for the outer surface of the insertion portion 21. In this embodiment, the anti-slip portion 114 is formed planar with a material having elasticity. Under an external force applied from the outside of the cylinder 94, the planar inner circumferential wall as the anti-slip portion 114 undergoes elastic deformation to come into close contact with the outer circumferential wall of the insertion portion 21 so that the insertion portion 21 can be gripped.

With reference to FIGS. 7 through 16, a description will be made about a removal method of the tip cover 15 by the cover removal jig 16 and a cleaning method of the endoscope 12.

As illustrated in FIG. 7, the cylinder 94 of the cover removal jig 16 is applied to the outer sides of the tip cover 15 and insertion portion 21, and the working portion 93 is then fitted on the tip cover 15. At this time, the direction of the marker 95 is parallel to the planar portion 66 of the distal end structure part 24. The closed portion 74 in the tip cover 15 is brought at a distal end wall thereof into contact with the bottom portion 97. As a consequence, the insertion portion 21, tip cover 15 and cover removal jig 16 change from the state illustrated in FIGS. 7 and 10 into the state illustrated in FIGS. 11, 12 and 14.

The first protrusion 101 is inserted into the indented edge portion 78B of the tip cover 15. The second protrusion 103 is brought close to or into contact with the distal end-side cover portion 102 of the distal end-side edge portion 78C of the tip cover 15. The rotating circumferential wall 75 of the tip cover 15 is supported in contact with the inner circumferential wall of the enclosing portion 91. At this time, the enclosing portion 91 is movable relative to the rotating circumferential wall 75 about the central axis C.

In this state, as illustrated in FIG. 12, the operator holds the grip handle 92 of the cover removal jig 16 by one of the hands, for example, by the left hand, and grips the insertion portion 21 via the cylinder 94 by the other hand, for example, by the right hand. The positions of fingers of the other hand are indicated by circular arcs of two-dot chain line. At the entire inner circumferential wall or the anti-slip portion 114, the cylinder 94 can exert a grip force on the insertion portion 21. In this state, the working portion 93 and grip handle 92 of the cover removal jig 16 are rotated relative to the insertion portion 21 about the central axis C in a direction indicated by arrow R in FIGS. 7 and 11. As a consequence, the pressing portion 101A comes into contact with the pressed portion 109 (see FIG. 5) between the indented edge portion 78B and the right-side edge portion 78A of the opening edge portion 78 in the tip cover 15, and presses the pressed portion 109. Moreover, the enclosing portion 91 of the cover removal jig 16 rotates relative to the rotating circumferential wall 75 of the tip cover 15.

Figure 15:
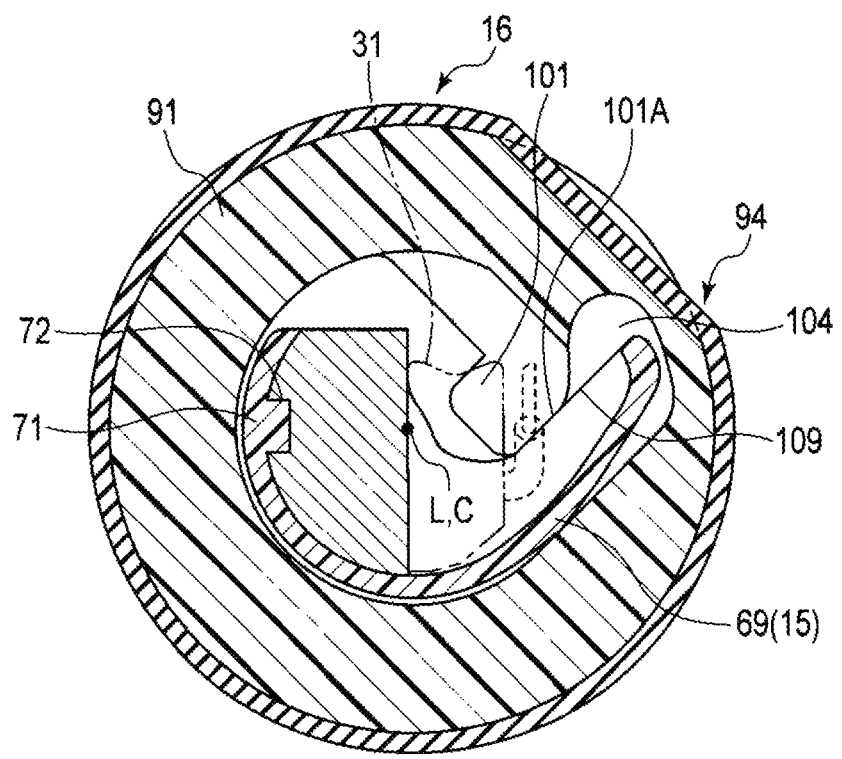
FIG. 15 is a cross-sectional view of the cover removal jig, distal end structure part and tip cover of FIG. 12 along line F15-F15, and is a cross-sectional view illustrating a state after having caused the working portion to rotate relative to the insertion portion.
Figure 16:
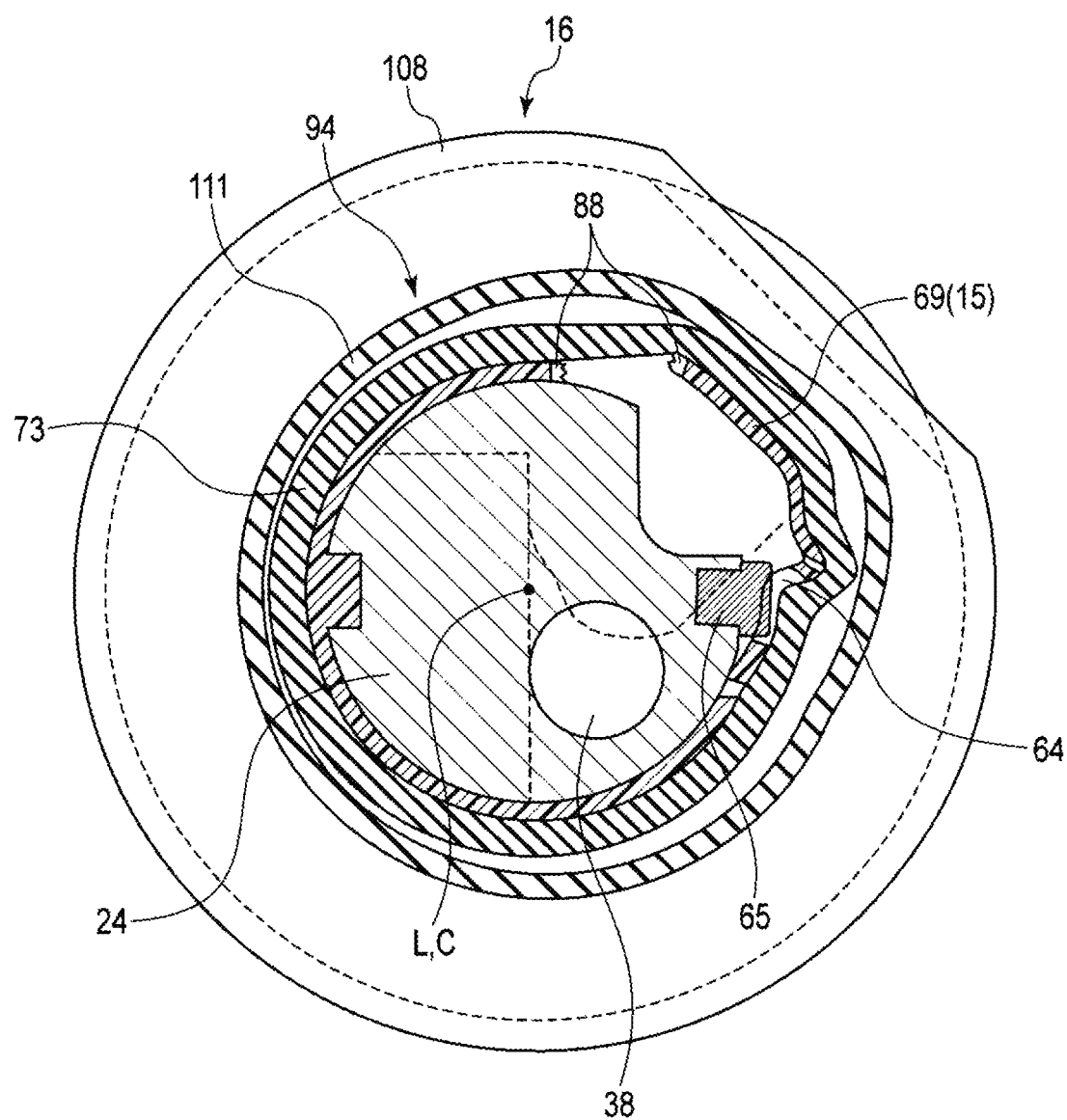
FIG. 16 is a cross-sectional view of the cover removal jig, distal end structure part and tip cover of FIG. 12 along line F16-F16, and is a cross-sectional view illustrating a state after having caused the working portion to rotate relative to the insertion portion.

At this time, the guide protrusion 71 of the tip cover 15 remains fitted in the guide groove 72 of the distal end structure part 24 as illustrated in FIGS. 15 and 16. The guide protrusion 71, therefore, restricts movements of the cover main body 69 relative to the distal end structure part 24 about the central axis C.

Figure 13:
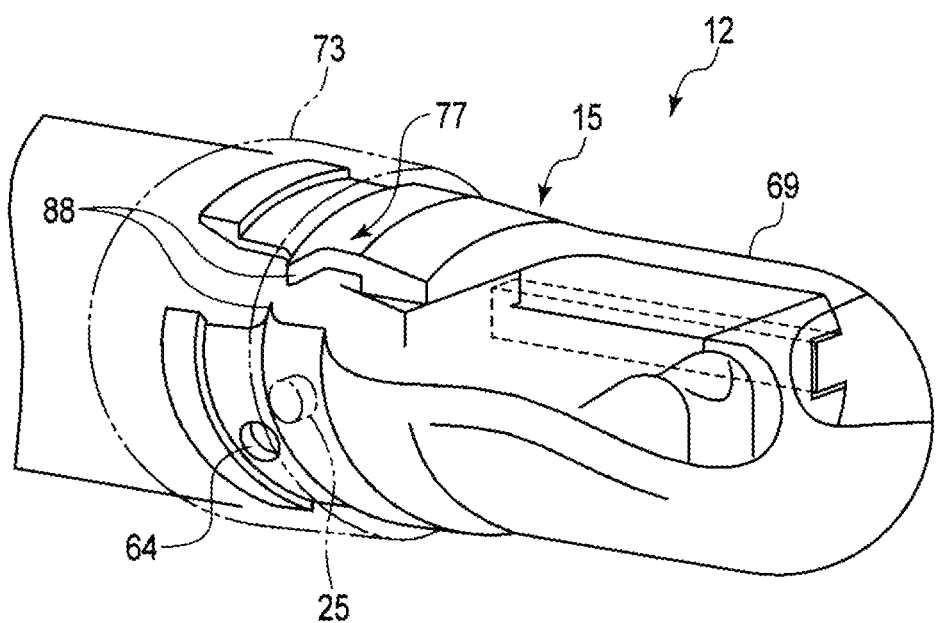
FIG. 13 is a perspective view illustrating a state that in the distal end structure part and tip cover of FIG. 2, a weakened portion of the tip cover has been broken off by the cover removal jig.
Figure 14:
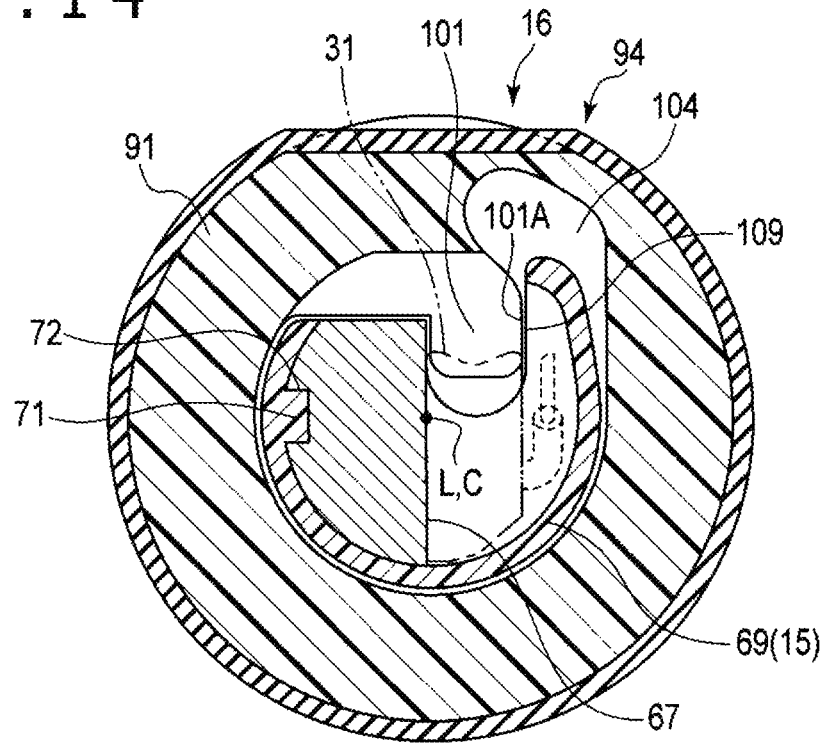
FIG. 14 is a cross-sectional view of the cover removal jig, distal end structure part and tip cover of FIG. 12 along line F14-F14, and is a cross-sectional view illustrating a state before causing a working portion to rotate relative to the insertion portion.

Accordingly, the quantity of an operating force by the cover removal jig 16 is applied to the connecting portion 88 between the slits 87, 87 of the tip cover 15, which opposes the first protrusion 101 of the cover removal jig 16, via the pressed portion 109, right-side edge portion 78A and proximal end-side edge portion 78E. As a consequence, a stress concentrates on the weakened portion 77 of the tip cover 15 so that the connecting portion 88 breaks off as illustrated in FIG. 13. By the break-off of the connecting portion 88, the tip cover 15 and cover removal jig 16 change from the state illustrated in FIG. 14 into the state illustrated in FIGS. 15 and 16, whereby with the guide protrusion 71 of the tip cover 15 still remaining fitted in the guide groove 72 of the distal end structure part 24, a portion of the annular part 76, the portion including the engagement hole 64, moves in the circumferential direction. At this time, the engagement of the engagement hole 64 of the tip cover 15 with the engagement pin 65 can be released by a driving force resulting from the break-off of the connecting portion 88. Hence, the break-off of the weakened portion 77 and the release of the engagement between the engagement pin 65 and the engagement hole 64 can be effected substantially at the same time.

It is to be noted that as illustrated in FIG. 15, the right-side edge portion 78A enters the receiving recess 104 of the cover removal jig 16. When the cover removal jig 16 is rotated further in this state relative to the distal end structure part 24 and tip cover 15 in the direction indicated by arrow R in FIG. 11, the operator of the cover removal jig 16 is then required to apply a force to bend the right-side edge portion 78A. Therefore, the enclosing portion 91 of the cover removal jig 16 becomes difficult to slide about the central axis C relative to the rotating circumferential wall 75 of the tip cover 15. The operator of the cover removal jig 16 perceives this state. When the cover removal jig 16 is rotated relative to the distal end structure part 24 and tip cover 15 in the direction indicated by arrow R, the operator of the cover removal jig 16, therefore, feels a certain resistance until as illustrated in FIG. 13, the connecting portion 88 is broken off and the engagement between the engagement pin 65 and the engagement hole 64 is released. The resistance then decreases, and subsequently, the operator feels a resistance again. By feeling the second resistance, the operator can perceive that the break-off of the connecting portion 88 has been completed.

Relative to the tip cover 15 with a break-off portion formed by the breaking of the weakened portion 77, the cover removal jig 16 is then pulled off along the longitudinal direction L in the direction C1 toward the distal end. As the weakened portion 77 has been broken, the operator can remove the tip cover 15 by grasping it with fingers, tongs or the like. In this manner, the tip cover 15 can be readily removed with attention being also paid to hygiene while assuring safety for operators, for example, a surgeon and surgical staff. It is to be noted that depending upon broken conditions, the tip cover 15 may separate together with the cover removal jig 16 from the distal end structure part 24. The removed tip cover 15 is discarded.

Figure 11:
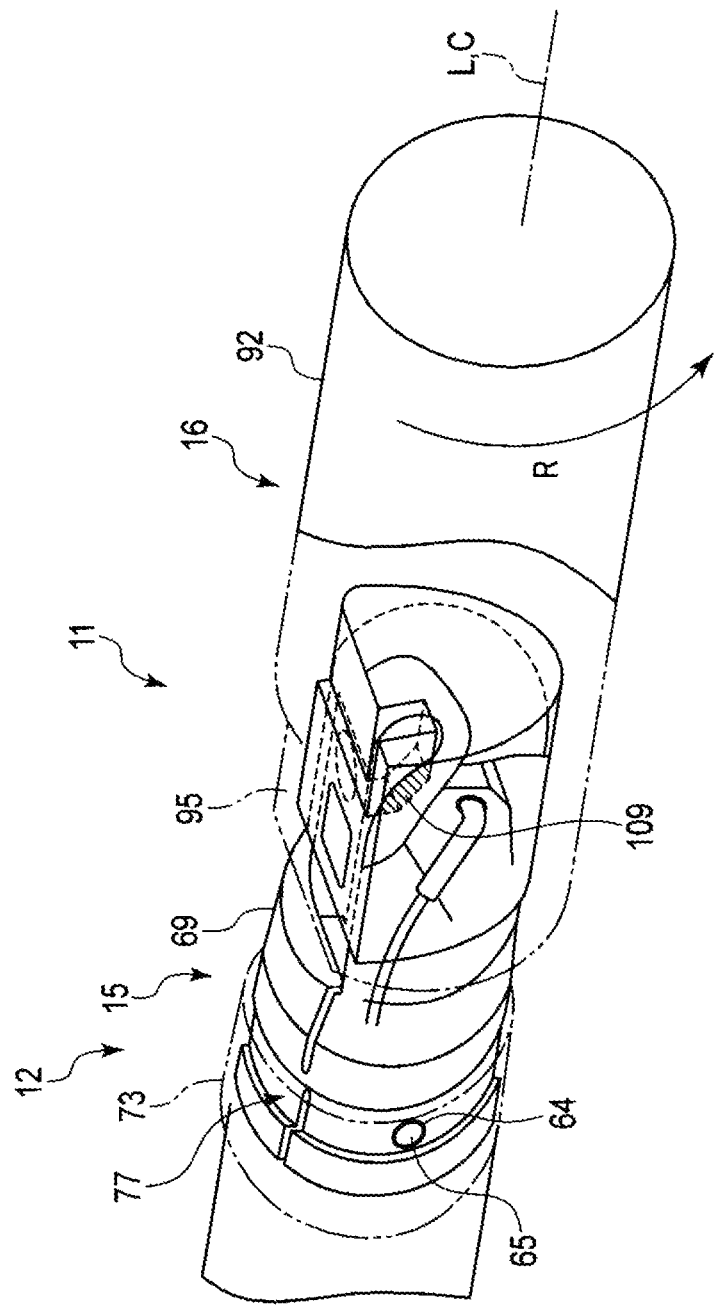
FIG. 11 is a perspective view illustrating, with omission of the cylinder, a state that the cover removal jig has been applied to the distal end structure part and tip cover of FIG. 10.

When the cover removal jig 16 is rotated relative to the tip cover 15 in a direction, which is opposite to the direction indicated by arrow R in FIGS. 7 and 11, in the state that the cover removal jig 16 is fitted on the tip cover 15, the first protrusion 101 of the cover removal jig 16 presses the wall of the accommodation space 67. Further, the second protrusion 103 remains in contact with the outer wall of the tip cover 15 in the vicinity of the distal end-side cover portion 102 and left-side edge portion 78D of the distal end-side edge portion 78C in the tip cover 15. The operator is, therefore, prevented from rotating, by mistake, the cover removal jig 16 in the direction opposite to the direction indicated by arrow R.

The endoscope 12 from which the tip cover 15 has been removed, in other words, the insertion portion 21 including the distal end structure part 24, the control section 22 and the universal cord 23 are appropriately cleaned, disinfected and sterilized and are provided for reuse. As the tip cover 15 has been removed from the distal end structure part 24 at this time, it is easy to clean not only a vicinity of the lighting window 45 of the illumination optical system and a vicinity of the observation window 46 of the observation optical system 37 but also the instrument insertion channel 38 and rocking mechanism 54.

This embodiment can bring about advantageous effects as will be described hereinafter. The cover removal jig 16 for the endoscope 12 is useful in removing the tip cover 15 applied on the distal end of the insertion portion 21 of the endoscope 12. The cover removal jig 16 has the enclosing portion 91 and the cylinder 94. The enclosing portion 91 is applied to the tip cover 15 to cover the circumference of the tip cover 15, and has a portion engageable with the tip cover 15. The cylinder 94 is connected to the enclosing portion 91, and has such elasticity as enabling the cylinder 94 to come into close contact with a part of the outer surface of the insertion portion 21.

According to this configuration, the cover removal jig 16 can be brought into close contact with the outer surface of the insertion portion 21 owing to the inclusion of the cylinder 94 having elasticity so that, upon removal of the tip cover 15 after use of the endoscope 12 and before cleaning of the same, the hand which is holding the insertion portion 21 can be prevented from slipping on the insertion portion 21. As a consequence, it is possible to facilitate the application of a force to the insertion portion 21 and enclosing portion 91 upon rotating the enclosing portion 91 relative to the insertion portion 21, and therefore to improve the workability upon removal by the operator.

The cylinder 94 is disposed extending from the enclosing portion 91 in the direction along the longitudinal direction L of the insertion portion 21. According to this configuration, the cylinder 94 is disposed integrally with the enclosing portion 91. It is, therefore, possible to decrease the number of components compared with disposing the cylinder 94 as a discrete member from the enclosing portion 91. As a consequence, the cover removal jig 16 is easy to handle by the operator.

The cylinder 94 has, on the inner circumferential wall thereof, the anti-slip portion 114 that acts as a slip resistant element for the outer surface of the insertion portion 21. According to this configuration, the cylinder 94 can be also used as a slip resistant element for the insertion portion 21 of the endoscope 12, and the operator's hand can be prevented from slipping on the insertion portion 21. As a consequence, it is possible to improve the workability upon removal of the tip cover 15 by the operator.

The cover removal jig 16 has the grip handle 92, which is disposed in continuation with the enclosing portion 91 on the side opposite to the side where the cylinder 94 is connected, and can be gripped by the operator. According to this configuration, the disposition of the grip handle 92 can facilitate operation by the operator, and therefore can improve the workability upon removal of the tip cover 15 by the operator.

The grip handle 92 includes, on the outer circumferential wall thereof, the third anti-slip portion 96 as a slip resistant element for the operator's hand. According to this configuration, the hand which is holding the grip handle 92 is prevented from slipping upon rotation of the cover removal jig 16 by the operator relative to the insertion portion 21, and therefore the workability upon removal of the tip cover 15 by the operator can be improved.

The outer diameter of the grip handle 92 is greater than that of the insertion portion 21. According to this configuration, it is possible to facilitate the application of a force to the grip handle 92 when the operator holds the grip handle 92. As a consequence, the workability can be improved upon rotation of the cover removal jig 16 by the operator relative to the insertion portion 21.

The enclosing portion 91 and the cylinder 94 rotate about a common axis extending along the central axis C of the insertion portion 21. According to this configuration, the enclosing portion 91 and the cylinder 94 do not interfere with a part of the tip cover 15 upon rotating them about the central axis C of the insertion portion 21, so that the removal work of the tip cover 15 can be smoothly conducted.

Descriptions will hereinafter be made about modifications in which parts of the above-described embodiment are modified. In the following modifications, the descriptions will be made primarily about those which are different from the corresponding ones in the above-described embodiment, and illustrations or descriptions will be omitted about those which are common to both.

Figure 17:
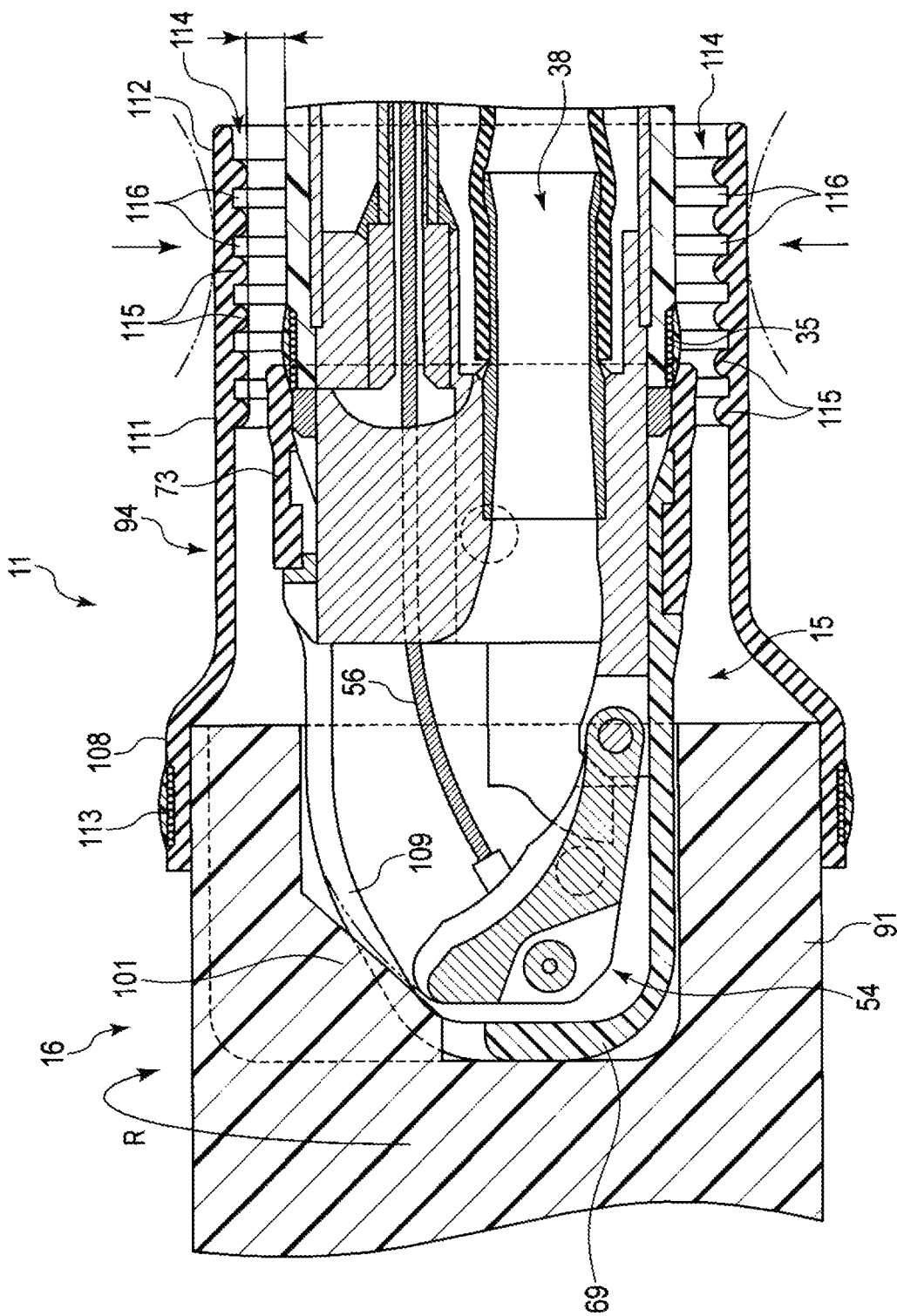
FIG. 17 is a cross-sectional view illustrating a distal end structure part, a tip cover and a cover removal jig in an endoscope system according to a first modification of the embodiment as taken on a plane along a central axis.

First Modification:

With reference to FIG. 17, a description will be made about an endoscope system 11 according to a first modification. In the first modification, the shape of an anti-slip portion 114 formed on the inner circumferential wall of the enclosing portion 91 of the cover removal jig 16 is different from that in the above-described embodiment.

The anti-slip portion 114 is configured of a plurality of annular convex portions 115 formed integrally with the cylinder 94 on the inner circumferential wall of the cylinder 94, and a plurality of concave portion 116 disposed between the convex portions 115. In other words, the anti-slip portion 114 in this modification is configured of a plurality of concavities and convexities formed on the inner circumferential wall of the cylinder 94. The annular convex portions 115 are disposed such that they are placed side by side at equal intervals in the direction of the central axis C. The convex portions 115 each have a semicircular cross-sectional shape. The concave portions 116 make up a fluid catch, which can receive and hold therein body fluids and debris that adhere the insertion portion 21 and tip cover 15 and may cause slipping.

A description will be made about operation of the cover removal jig 16 in this modification and the endoscope system 11 including the cover removal jig 16.

When the cylinder 94 is held at outer circumferential portions thereof by operator's fingers as indicated by circular arcs of two-dot chain line in FIG. 17 upon removing the tip cover 15 by using the cover removal jig 16 in this modification, the cylinder 94 is lightly pressed so that the annular convex portions 115 located on the inner circumferential wall of the cylinder 94 are brought into contact with the insertion portion 21, wound thread coil 35 and tip cover 15, specifically holding ring 73. The annular convex portions 115 are disposed at equal intervals along the central axis C, and therefore can appropriately undergo deformation and can come into close contact with the insertion portion 21, specifically the wound thread coil 35, the cover main body 69 and the holding ring 73 although the insertion portion 21 includes stepped portions such as the wound thread coil 35 and tip cover 15, specifically holding ring 73 in this modification.

This modification is also effective even if body fluids and debris have adhered the surfaces of the insertion portion 21 and tip cover 15. Described specifically, when the insertion portion 21 is gripped first, the annular convex portions 115 come into contact with the insertion portion 21 and tip cover 15 and then undergo slipping due to such deposits to move such that they sweep the surfaces of the insertion portion 21 and tip cover 15 over a small distance. As a consequence, the deposits, specifically the body fluids and debris are removed from the surface of the insertion portion 21, specifically the tip cover 15 and are held in the concave portions 116. The anti-slip portion 114 can, therefore, exert a sufficient gripping force on the insertion portion 21 after the annular convex portions 115 have undergone slipping over a small distance as described above. Owing to the gripping force by the anti-slip portion 114, the operator can readily rotate the working portion 93 of the cover removal jig 16 by a small force relative to the insertion portion 21 without slipping of the hand, which is holding the insertion portion 21, on the insertion portion 21. As a consequence, the weakened portion 77 of the tip cover 15 can be easily broken. After the breaking of the weakened portion 77, the operator can remove the tip cover 15 from the distal end structure part 24.

In this modification, the anti-slip portion 114 is configured of the concavities and convexities formed on the inner circumferential wall of the cylinder 94. According to this configuration, owing to the disposition of the convexities, the convexities can be brought into close contact with the insertion portion 21 and tip cover 15 despite the existence of the stepped portions on the surfaces of the insertion portion 21 and tip cover 15. Further, upon rotation of the enclosing portion 91 relative to the insertion portion 21, the convexities slide over a small distance on the surfaces of the insertion portion 21 and tip cover 15 so that body fluids and debris adhered on the surfaces of the insertion portion 21 and tip cover 15 can be removed. On the other hand, the disposition of the concavities makes it possible to hold therein the body fluids and debris removed as described above. As a consequence, the anti-slip portion 114 can exert a sufficient gripping force on the outer surface of the insertion portion 21. Therefore, the workability for the operator can be improved.

Figure 18:
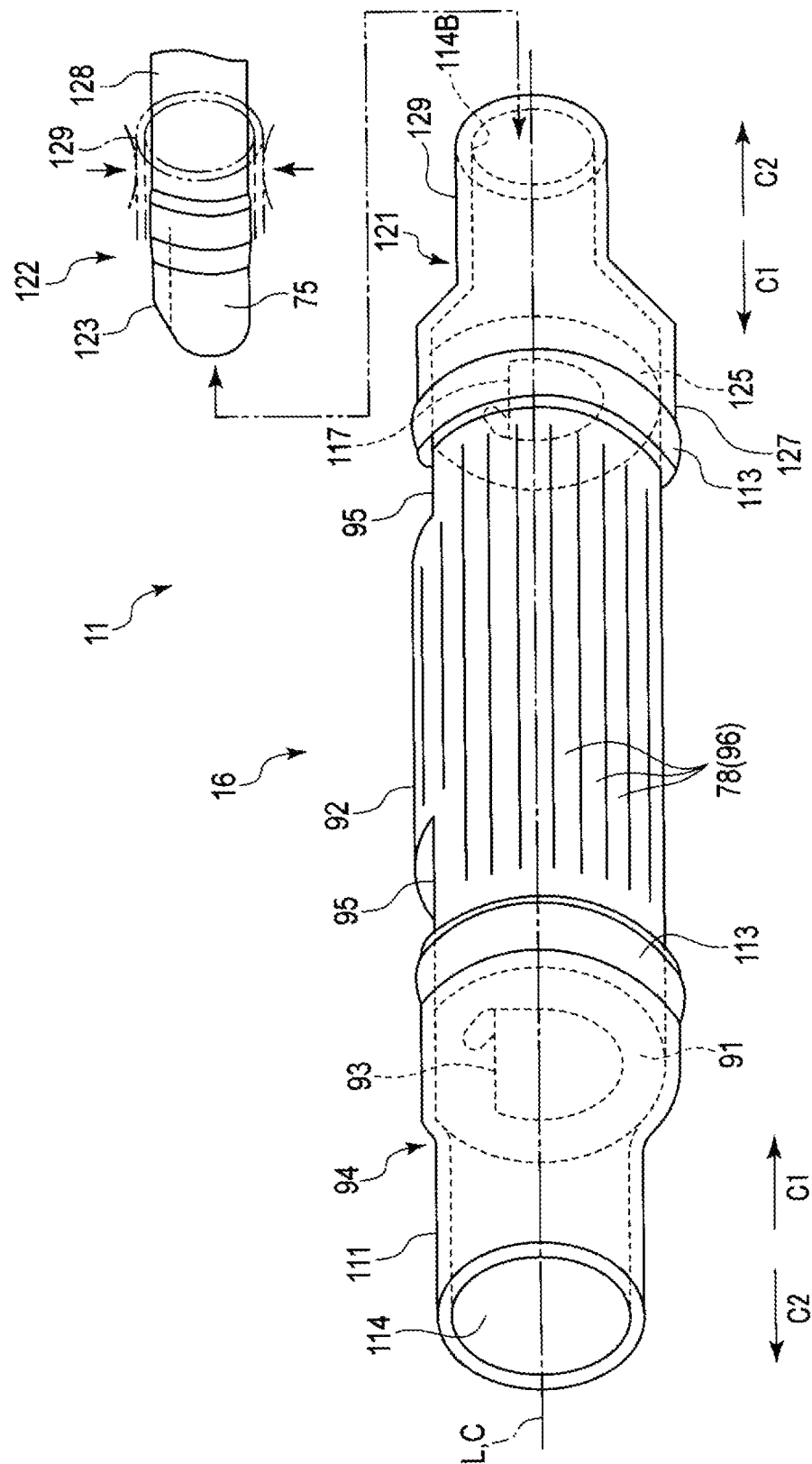
FIG. 18 is a perspective view of a cover removal jig according to a second modification of the embodiment.
Figure 19:
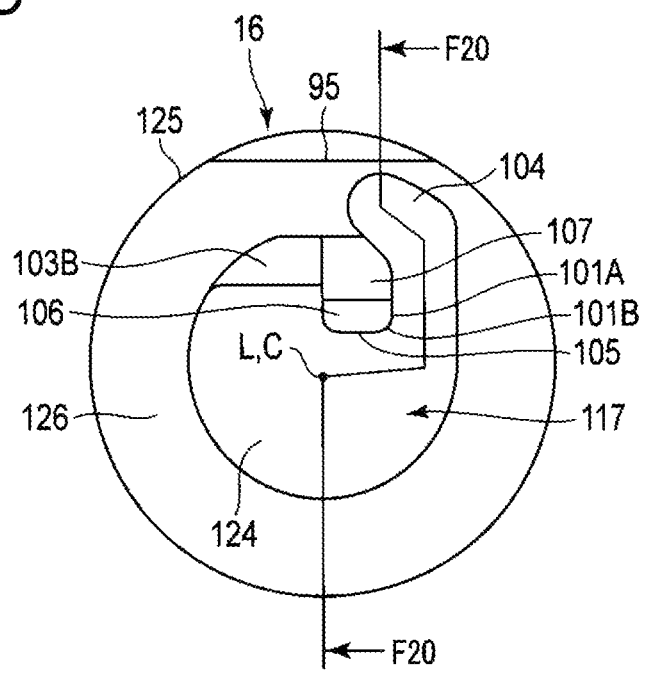
FIG. 19 is a front view of a second working portion in the cover removal jig of FIG. 18, with a second cylinder having been detached, as viewed from a front.
Figure 20:
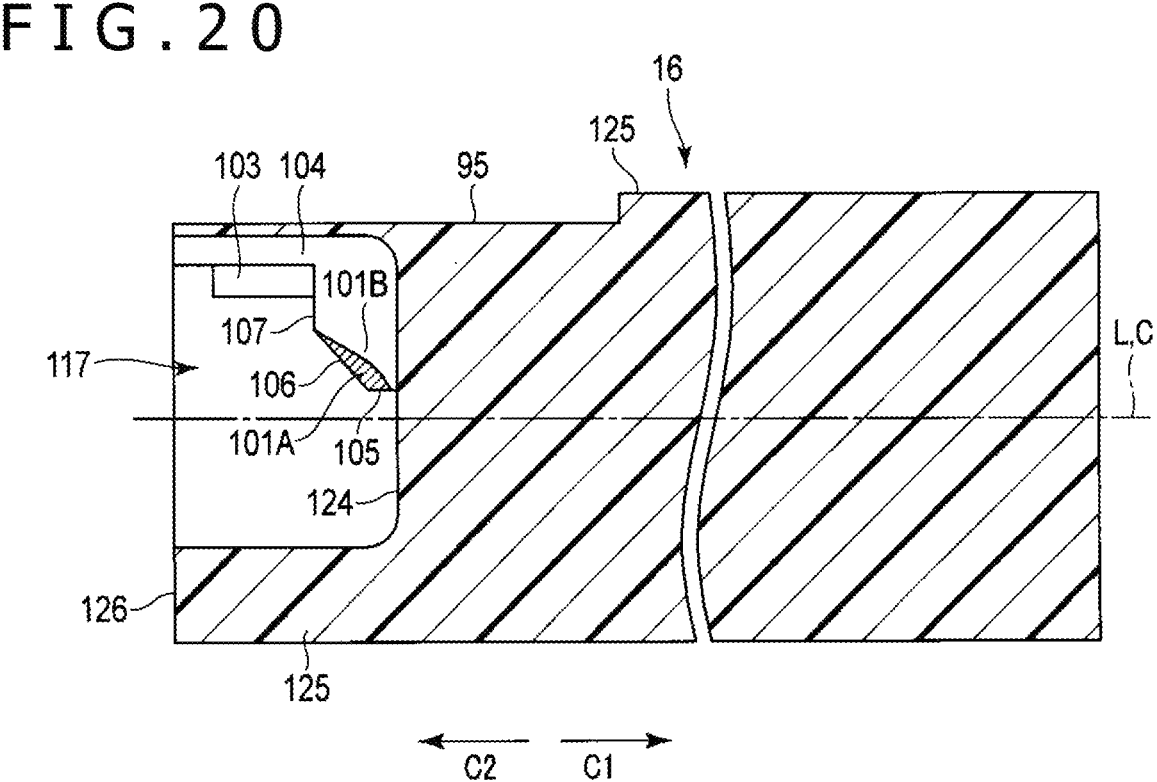
FIG. 20 is a cross-sectional view taken along line F20-F20 in FIG. 19.

Second Modification:

With reference to FIGS. 18 to 20, a description will be made about an endoscope system 11 according to a second modification. The second modification is different from the above-described embodiment in that a cover removal jig 16 has, in addition to the working portion 93, specifically the enclosing portion 91, a second working portion 117, specifically a second enclosing portion 125 and also in that the cover removal jig 16 has, in addition to the cylinder 94, a second cylinder 121. Therefore, the cover removal jig 16 of this modification can be used for both of the removal of a tip cover 15 from an adult endoscope 12 having a normal diameter and the removal of an additional tip cover, specifically a second tip cover 123 from a pediatric endoscope having a smaller diameter than the normal diameter, specifically a second endoscope 122.

The cover removal jig 16 has the columnar grip handle 92 as a part to be held by an operator, the working portion 93 disposed on one of the end portions of the grip handle 92, the cylinder 94 connected to the below-described enclosing portion 91 of the working portion 93 and having elasticity, the marker 95 arranged on the grip handle 92 and working portion 93 at a position adjacent to the cylinder 94, the second working portion 117 disposed on the other end portion of the grip handle 92, the second cylinder 121 connected to the below-described second enclosing portion 125 of the second working portion 117 and having elasticity, and an additional marker 95 arranged on the grip handle 92 and the second working portion 117 at a position adjacent to the second cylinder 121. The outer diameter of the grip handle 92 is greater than that of the insertion portion 21 and that of a second insertion portion 128 of the second endoscope 122. The grip handle 92, working portion 93, cylinder 94 and additional marker 95 are configured as in the above-described embodiment.

The additional marker 95 has a similar shape as the marker 95. By touching the additional marker 95, the operator can perceive an angle of the cover removal jig 16 in the circumferential direction about the axis in the longitudinal direction L.

The second working portion 117 has substantially the same configuration as the working portion 93 although they are different in size. As illustrated in FIGS. 19 and 20, the second working portion 117 has a second bottom portion 124 that is brought into contact with a distal end of the second tip cover 123, the cylindrical second enclosing portion 125 that extends from the second bottom portion 124 and can cover a circumference of the second tip cover 123, a second end face 126 disposed at a distal end of the second enclosing portion 125, a first protrusion 101B that is fitted in a U-shaped indented edge portion 78B at an opening edge portion 78 of the second tip cover 123, a second protrusion 103B that is fitted on a distal end-side cover portion 102 of a cover main body 69, the distal end-side cover portion 102 being flush with a planar portion 66 of a distal end structure part 24, and a receiving recess 104 in which a portion of a right-side edge portion 78A of an opening edge portion 78 of the broken second tip cover 123 is placed. The first protrusion 101B or a protrusion has a stepped portion 105 that extends in the direction of the central axis C, an inclined portion 106 that is inclined away from the central axis C progressively in the direction C2 toward the proximal end, and a top wall portion 107 that is disposed on a side in the direction C2 toward the proximal end. The first protrusion 101B which is a portion to engage the second tip cover 123 is integrally formed with the second enclosing portion 125, and in other words, is disposed as a portion of the second enclosing portion 125.

The second enclosing portion 125 has an inner diameter formed slightly greater than the diameter of the second tip cover 123 as defined by a rotating circumferential wall 75. The first protrusion 101B has a width formed slightly smaller than that of the second indented edge portion 78B of the second tip cover 123. As illustrated in FIG. 20, the first protrusion 101B of the cover removal jig 16 has a second pressing portion 101A. The second pressing portion 101A is brought into contact with a pressed portion 109 (see FIG. 5) between the second indented edge portion 78B and the right-side edge portion 78A of the opening edge portion 78 in the second tip cover 123.

As illustrated in FIG. 18, the second cylinder 121 has a second reduced diameter portion 129, which is reduced in diameter on a side in the direction C2 toward the proximal end, specifically on a side opposite to the end portion connected to the second enclosing portion 125. The second cylinder 121 has an inner diameter formed slightly greater than an outer diameter of the second tip cover 123 for the second endoscope 122. A slight clearance is, therefore, left between the second tip cover 123 and the second cylinder 121 in a state that the insertion portion 21 is covered by the second cylinder 121.

The second cylinder 121 is formed with the same material as the cylinder 94. To facilitate discrimination between the cylinder 94 and the second cylinder 121, the second cylinder 121 may have a color different from the cylinder 94. The second cylinder 121 has a second sleeve portion 127, which is firmly fixed by a second wound thread coil 113 formed with a thread wound on and around an outer circumference of the second cylinder 121, so that the second sleeve portion 127 is integrated with the second enclosing portion 125. The second wound thread coil 113 is covered at a surface thereof with a resin. On an inner circumferential wall of the second cylinder 121, an anti-slip portion 114B is formed as a slip resistant element for an outer surface of the second insertion portion 128. In this modification, the anti-slip portion 114B is formed planar with a material having elasticity. Under an external force applied from the outside of the second cylinder 121, the planar inner circumferential wall as the anti-slip portion 114B undergoes elastic deformation to come into close contact with an outer circumferential wall of the second insertion portion 128.

In this modification, the working portion 93 and the second working portion 117 are disposed independently of each other, but are not limited to this arrangement. The cover removal jig 16 may omit the bottom portion 97 (see FIG. 9) and the second bottom portion 124 (see FIG. 20), and may have a structure, specifically a hollow structure that an inner bore of the enclosing portion 91 and an inner bore of the second enclosing portion 125 are communicated together. This structure can realize a cover removal jig 16, which can be easily cleaned, is light in weight, and can be easily dried after cleaning.

A similar method as the removal method described above in the embodiment can be followed to remove the tip cover 15 from the endoscope 12 by using the working portion 93 and cylinder 94 of the cover removal jig 16 of this modification. Further, substantially the same method as the removal method of the working portion 93 and cylinder 94 as described above in the embodiment can be also followed to remove the second tip cover 123 from the second endoscope 122 by using the second working portion 117 and second cylinder 121 in this modification. In addition, a similar method as the cleaning method of the endoscope 12 as described above in the embodiment can be followed to clean the endoscope 12 or second endoscope 122 after the removal of the tip cover 15 or second tip cover 123.

According to this modification, the cover removal jig 16 has the second enclosing portion 125 disposed continuously on the grip handle 92 on the side opposite to the side where the grip handle 92 is in continuation with the enclosing portion 91, and the second enclosing portion 125 is applied to the second tip cover 123 to cover the circumference of the second tip cover 123, the dimeter of which is different from that of the tip cover 15, and has the portion that is engageable with the second tip cover 123. According to this configuration, the single cover removal jig 16 can be commonly used for the removal of the tip cover 15 for the endoscope 12, the diameter of the tip cover 15 being different, so that the cover removal jig 16 can have improved versatility.

Figure 21:
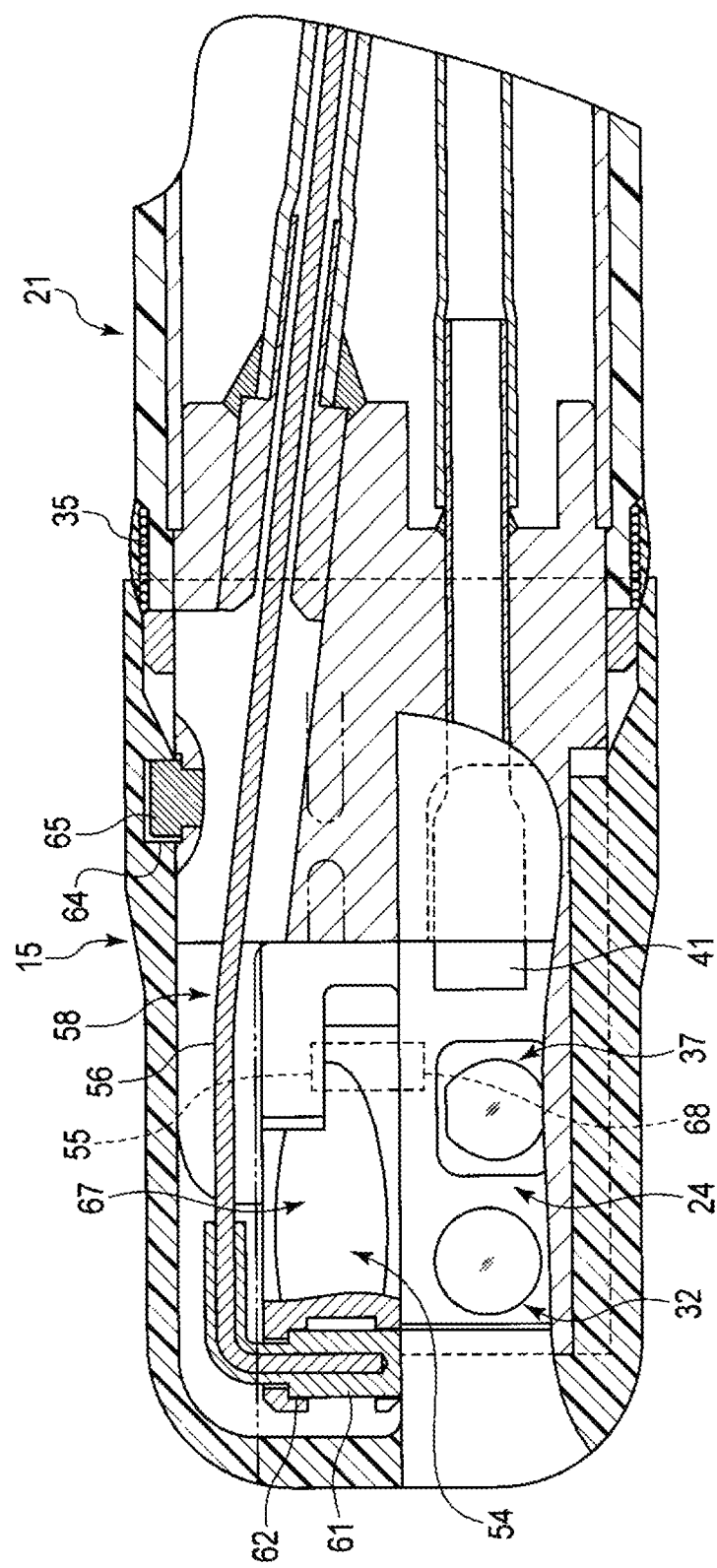
FIG. 21 is a cross-sectional view illustrating a tip cover and a distal end structure part in a third modification of the embodiment as taken on a plane along a central axis.

Third Modification:

With reference to FIG. 21, a description will be made about an endoscope system 11 according to a third modification. In the third modification, a tip cover 15 is configured with a structure that the cover main body 69 and holding ring 73 in the above-described embodiment have been integrated. The tip cover 15 is formed with a similar material as that of the cover main body 69 in the above-described embodiment. Removal of the tip cover 15 can be conducted in a similar manner as the method described above in the embodiment.

According to this modification, the structure of the tip cover 15 can be simplified to decrease the number of components, and as a consequence the manufacturing cost can be cut down.

Figure 22:
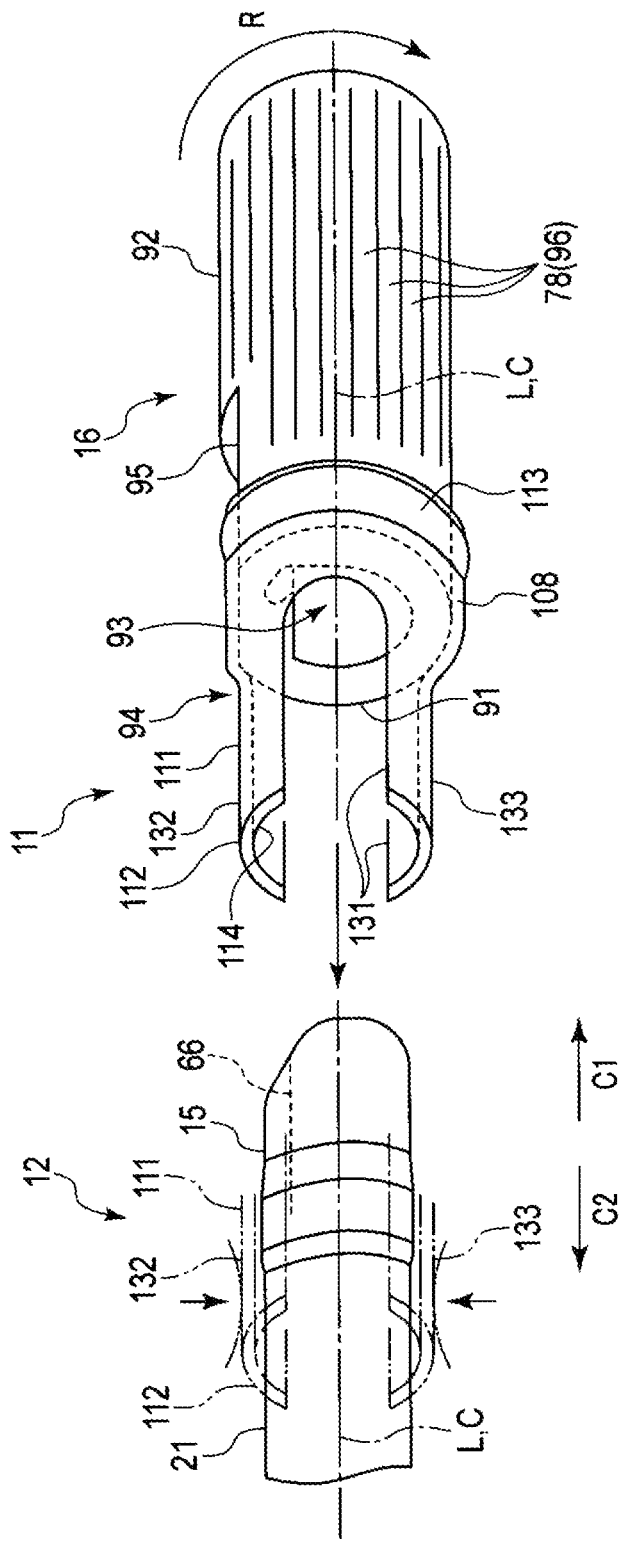
FIG. 22 is a perspective view illustrating a tip cover, a distal end structure part and a cover removal jig in a fourth modification of the embodiment.

Fourth Modification:

With reference to FIG. 22, a description will be made about an endoscope system 11 according to a fourth modification. In the shape of a cylinder, the fourth modification is different from the above-described embodiment.

As illustrated in FIG. 22, a cylinder 94 has a reduced diameter portion 111, which is reduced in diameter on a side in the direction C2 toward the proximal end, specifically on a side opposite to the end portion connected to the enclosing portion 91. The cylinder 94 has a pair of notched portions 131 or indentations at opposing parts thereof at the reduced diameter portion 111. In other words, the cylinder 94 has a shape including a first quonset-shaped portion 132 and a second quonset-shaped portion 133 that opposes the first quonset-shaped portion 132. The paired notched portions 131 are formed from viewpoints of improving the visibility of an interior of the working portion 93, saving the material required for use in forming the cylinder 94, and the like. Except for the paired notched portions 131, the cylinder 94 has the same structure as the cylinder 94 described above in the embodiment, and is formed with the same material as in the above-described embodiment.

With reference to FIG. 22, a description will be made about a removal method of the tip cover 15 by the cover removal jig 16 and a cleaning method of an endoscope.

The cylinder 94 of the cover removal jig 16 is applied to the outer sides of the tip cover 15 and insertion portion 21, and the working portion 93 is then fitted on the tip cover 15. At this time, the direction of the marker 95 is parallel to the planar portion 66 of the distal end structure part 24. The closed portion 74 in the tip cover 15 is brought at a distal end wall thereof into contact with the bottom portion 97. As a consequence, the insertion portion 21, tip cover 15 and cover removal jig 16 assume a state similar to that illustrated in FIGS. 11 and 12.

The first protrusion 101 is inserted into the indented edge portion 78B of the tip cover 15. The second protrusion 103 is brought close to or into contact with the distal end-side cover portion 102 of the distal end-side edge portion 78C of the tip cover 15. The rotating circumferential wall 75 of the tip cover 15 is supported in contact with the inner circumferential wall of the enclosing portion 91. At this time, the enclosing portion 91 is movable relative to the rotating circumferential wall 75 about the central axis C.

In this state, as illustrated in FIG. 22, the operator holds the grip handle 92 of the cover removal jig 16 by one of the hands, for example, by the left hand, and presses the first quonset-shaped portion 132 of the cylinder 94 by the thumb or the like of the other hand, for example, the right hand, and presses the second quonset-shaped portion 133 by the index finger or the like of the other hand, for example, the right hand. The positions of the fingers of the other hand are indicated by circular arcs of two-dot chain line. As a consequence, the insertion portion 21 is gripped so that it is held between the first quonset-shaped portion 132 and the second quonset-shaped portion 133. In this state, the working portion 93 and grip handle 92 of the cover removal jig 16 are rotated relative to the insertion portion 21 about the central axis C in a direction indicated by arrow R in FIG. 22. As a consequence, the pressing portion 101A comes into contact with the pressed portion 109 (see FIG. 5) between the indented edge portion 78B and the right-side edge portion 78A of the opening edge portion 78 in the tip cover 15, and presses the pressed portion 109. Moreover, the enclosing portion 91 of the cover removal jig 16 rotates relative to the rotating circumferential wall 75 of the tip cover 15.

As a consequence, a stress concentrates on the weakened portion 77 of the tip cover 15 so that the connecting portion 88 breaks off as illustrated in FIG. 13, and the engagement of the engagement hole 64 of the tip cover 15 with the engagement pin 65 is released. After removal of the tip cover 15 the weakened portion 77 of which has been broken, the endoscope 12 is appropriately cleaned, disinfected and sterilized and is provided for reuse.

According to this modification, the cylinder 94 has the indentations or the notched portions 131 at positions deviated from the parts to be gripped by the operator. According to this configuration, the inclusion of the indentations in the cylinder 94 can improve the visibility of an interior of the enclosing portion 91, and can save the material required for use in forming the cylinder 94. Therefore, the operator is facilitated in finding the directions in which the enclosing portion 91 and the insertion portion 21 should be rotated, improved workability can be provided to the operator, and the manufacturing cost of the cover removal jig 16 can be cut down.

Figure 23:
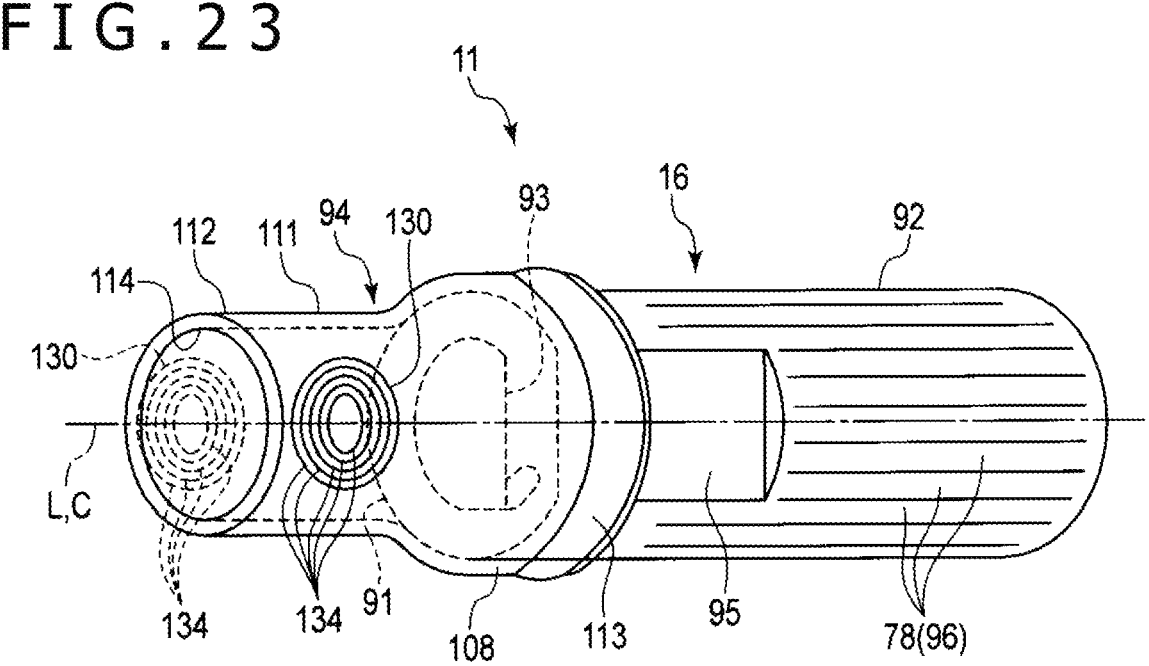
FIG. 23 is a perspective view illustrating a cover removal jig in a fifth modification of the embodiment.

Fifth Modification:

With reference to FIG. 23, a description will be made about an endoscope system 11 according to a fifth modification. The fifth modification is different from the above-described embodiment in that second anti-slip portions 130 are disposed on the outer surface of the cylinder 94.

The cylinder 94 has a reduced diameter portion 111, which is reduced in diameter on a side in the direction C2 toward the proximal end, specifically on a side opposite to the end portion connected to the enclosing portion 91. The cylinder 94 has the second anti-slip portions 130 in pair at the reduced diameter portion 111. One of the second anti-slip portions 130 opposes the other second anti-slip portions 130. In other words, the second anti-slip portions 130 are disposed in pair on both sides with the central axis C interposed therebetween. The paired second anti-slip portions 130 also function as markers that indicate positions where forces are to be applied from the outside when gripped by an operator.

The second anti-slip portions 130 are each configured of plural grooves 134 formed in an area of substantially the same size as a finger, for example, the thumb of the operator. The plural grooves 134 are formed, for example, in the form of double to quintuple rings so that they surround a central part of the area. The plural grooves 134 each have a circular or oval form. Except for the second anti-slip portions 130, the cylinder 94 has the same structure as the cylinder 94 described above in the embodiment, and is formed with the same material as in the above-described embodiment.

Similar removal and cleaning methods as in the above-described embodiment can be followed to remove the tip cover 15 by using the cover removal jig 16 and to clean the endoscope.

Referring to FIG. 23, a description will be made about operation of the cover removal jig 16 of this modification. In this modification, the second anti-slip portions 130 function as slip resistant elements for preventing the operator's hand from slipping on the cylinder 94 when the operator grips the cylinder 94. In addition, the second anti-slip portions 130 also function as markers that indicate where to hold the cylinder 94 when the operator grips the cylinder 94.

In this modification, the operator presses, for example, one of the second anti-slip portions 130 by the thumb and the other second anti-slip portion 130 by another finger such as the index finger, whereby an appropriate external force can be applied to the cylinder 94 to grip the insertion portion 21 by the cylinder 94. Moreover, the operator is not confused as to where to hold.

According to this modification, the cylinder 94 has the markers that indicate the positions where forces are to be applied from the outside. According to this configuration, when the operator is to grip the insertion portion by applying a force to the cylinder 94, external forces can be applied by using the markers as target positions. Therefore, the operator can proceed with the work without hesitation and a user-friendly cover removal jig 16 can be realized.

Figure 24:
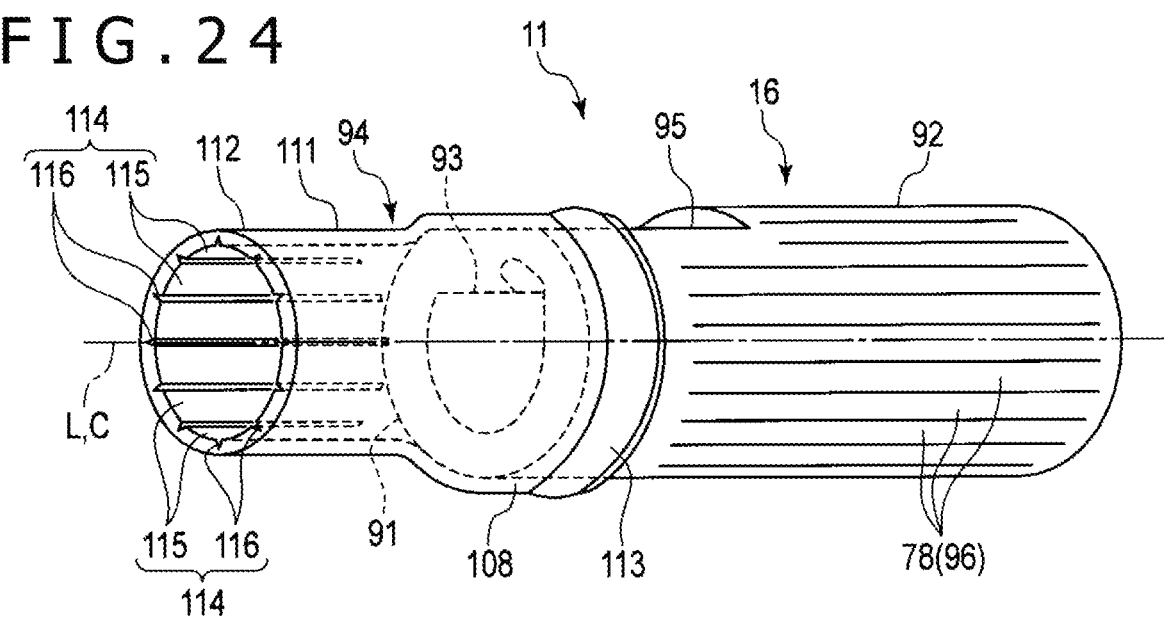
FIG. 24 is a perspective view illustrating a cover removal jig in a sixth modification of the embodiment.

Sixth Modification:

With reference to FIG. 24, a description will be made about an endoscope system 11 according to a sixth modification. In the shape of an anti-slip portion 114 formed on an inner circumferential wall of an enclosing portion 91 of a cover removal jig 16, the sixth modification is different from the above-described embodiment. In addition, the anti-slip portion 114 is configured of concavities and convexities, which extend in a direction different by 90° from that in the above-described first modification.

The anti-slip portion 114 is configured of a plurality of convex portions 115 formed integrally with the cylinder 94 on the inner circumferential wall of the cylinder 94, and a plurality of concave portions 116 disposed between the convex portions 115. In this modification, the anti-slip portion 114 is configured of the plural concavities and convexities formed on the inner circumferential wall of the cylinder 94. The convex portions 115 are formed of portions of the inner circumferential wall of the cylinder 94, the portions being other than the concave portions 116. The convex portions 115 each extend in the direction of the central axis C. The convex portions 115 each have a trapezoidal cross-sectional shape.

The concave portions 116 are disposed at equal intervals on the circumferential wall of the cylinder 94. In other words, these concave portions 116 are disposed at equal intervals about the central axis C. The concave portions 116 are each formed in the shape of a substantially V-shaped groove. The concave portions 116 each extend in the direction of the central axis C. The concave portions 116 make up a fluid catch, which can receive and hold therein body fluids, debris and the like that adhere the insertion portion 21 and tip cover 15 and may cause slipping.

A description will be made about operation of the cover removal jig 16 in this modification and the endoscope system 11 including the cover removal jig 16.

When the cylinder 94 is held at outer circumferential portions thereof by operator's fingers upon removing the tip cover 15 by using the cover removal jig 16 in this modification, the cylinder 94 is lightly pressed so that the annular convex portions 115 located on the inter circumferential wall of the cylinder 94 are brought into contact with the insertion portion 21, the wound thread coil 35, the cover 15, specifically holding ring 73, and the like. This modification is also effective even if body fluids and debris have adhered the surfaces of the insertion portion 21 and tip cover 15. Described specifically, when the insertion portion 21 is gripped first, the annular convex portions 115 come into contact with the insertion portion 21 and tip cover 15 and then undergo slipping due to such deposits to move such that they sweep the surfaces of the insertion portion 21 and tip cover 15 over a small distance. As a consequence, the deposits, specifically the body fluids and debris are removed from the surface of the insertion portion 21, specifically the tip cover 15 and are held in the concave portions 116. The anti-slip portion 114 can, therefore, exert a sufficient gripping force on the insertion portion 21 after the annular convex portions 115 have undergone slipping over a small distance as described above. Owing to the gripping force by the anti-slip portion 114, the operator can readily rotate the working portion 93 of the cover removal jig 16 by a small force relative to the insertion portion 21 without slipping of the hand, which is holding the insertion portion 21, on the insertion portion 21. Therefore, the breaking of the weakened portion 77 of the tip cover 15 makes it possible to remove the tip cover 15 from the distal end structure part 24.

According to this modification, the anti-slip portion 114 is configured of the concavities and convexities formed on the inner circumferential wall of the cylinder 94. According to this configuration, substantially the same advantageous effects as those available from the first modification can be brought about. In this modification, the concavities and convexities are disposed so that they are placed side by side in the circumferential direction about the central axis C. This direction in which the concavities and convexities are placed side by side is a direction along the direction in which the enclosing portion 91 and insertion portion 21 rotate. Accordingly, even if body fluids and debris have adhered the insertion portion 21 and tip cover 15, such body fluids and debris can be effectively held in the concave portions 116 so that the anti-slip portion 114 can produce a still greater gripping force.

Figure 25:
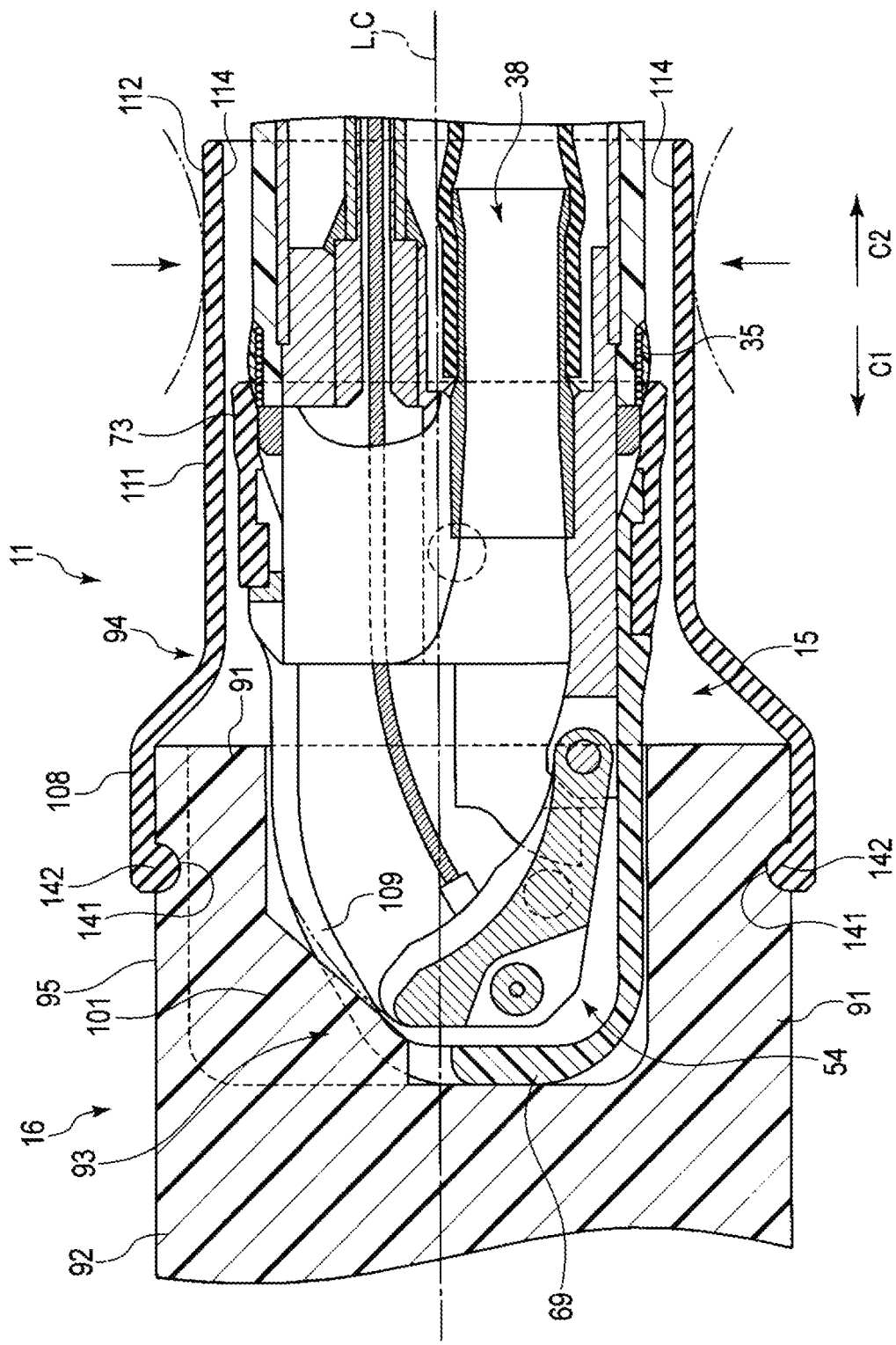
FIG. 25 is a cross-sectional view illustrating a cover removal jig in a seventh modification of the embodiment.

Seventh Modifications:

With reference to FIG. 25, a description will be made about an endoscope system 11 according to a seventh modification. In the manner of application of a cylinder 94 to a working portion 93, specifically an enclosing portion 91 of a cover removal jig 16, the seventh modification is different from the above-described embodiment.

The enclosing portion 91 has, on an outer circumferential wall thereof, a groove portion 141 formed in an annular shape about the central axis C. The groove portion 141 has a cross-sectional shape recessed in a semicircular shape. A below-described engagement portion 142 of the cylinder 94 can fit in the groove portion 141.

The cover removal jig 16 has the columnar grip handle 92 as a part to be gripped by an operator, the working portion 93 disposed on one of the end portions of the grip handle 92, the cylinder 94 connected to the below-described enclosing portion 91 of the working portion 93 and having elasticity, and the marker 95 arranged on the grip handle 92 and working portion 93. In this modification, no wound thread coil is disposed on the sleeve portion 108 of the cylinder 94 to fix the cylinder 94 on the enclosing portion 91.

The cylinder 94 has the sleeve portion 108 and a reduced diameter portion 111 reduced in diameter on a side in the direction C2 toward the proximal end, specifically on a side opposite to the end portion connected to the enclosing portion. The cylinder 94 has an inner diameter formed slightly greater than the outer diameter of the holding ring 73 of the tip cover 15. A slight clearance is, therefore, left between the holding ring 73 and the cylinder 94 in a state that the insertion portion 21 is covered by the cylinder 94.

The cylinder 94 is formed with a similar material as in the above-described embodiment. The sleeve portion 108 includes the engagement portion 142 protruding in an annular form inwardly of the cylinder 94. The engagement portion 142 has a semicircular shape in cross-section, and can fit in the groove portion 141 without clearance. Therefore, the cylinder 94 is connected or attached detachably to the enclosing portion 91 and rotatably to enclosing portion 91 about the central axis C. On the inner circumferential wall of the cylinder 94, an anti-slip portion 114 is formed as a slip resistant element for the outer surface of the insertion portion 21. The anti-slip portion 114 has a similar configuration as in the above-described embodiment.

A description will be made about operation of the cover removal jig 16 in this modification and the endoscope system 11 including the cover removal jig 16.

When removing the tip cover 15 with the cover removal jig 16 of this modification, the grip handle 92 held by one of the hands and the enclosing portion 91 connected to the grip handle 92 are rotated relative to the insertion portion 21, which is gripped by the other hand via the cylinder 94, as in the above-described embodiment. Here, the cylinder 94 is held stationary on the enclosing portion 91 via the engagement portion 142, so that a tension acts on the cylinder 94 in a twisting direction, in other words, in the circumferential direction about the central axis C. In this modification, the cylinder 94 is rotatably attached relative to the enclosing portion 91. If such a tension acts, the cylinder 94 can, therefore, rotate or revolve about the central axis C in a direction that relieves the tension.

Further, if the enclosing portion 91 is substantially rotated by the operator in a relatively short period of time, wrinkles may be formed on the cylinder 94, and the cylinder 94 may be pulled, at a part thereof on the side of the direction C2 toward the proximal end, specifically at the engagement portion 142, in a moment in the direction C2 toward the proximal end. On the other hand, the cylinder 94 is detachable from the enclosing portion 91. In such a case, the cylinder 94 may hence be allowed to come out of the groove portion 141 of the enclosing portion 91.

Therefore, the cylinder 94 is not broken, and in addition, a tension that acts on the cylinder 94 is prevented from impeding rotating operation of the working portion 93. It is to be noted that the cylinder 94, which has come out of the groove portion 141, can be readily attached or connected to the enclosing portion 91 if the operator brings it into engagement with the groove portion 141 again.

According to this modification, the cylinder 94 is detachably connected to the enclosing portion 91. If rotating operation of the enclosing portion 91 is conducted in a short period of time, for example, wrinkles may be formed at a part of the cylinder 94 so that the cylinder 94 may be pulled toward the insertion portion 21. According to the configuration described above, however, the cylinder 94 can still fall off from the enclosing portion 91 even if the cylinder 94 is pulled toward the insertion portion 21 and a tension acts on the cylinder 94 to a certain degree or higher. It is, therefore, possible to prevent a tension, which acts on the cylinder 94, from impeding rotation of the enclosing portion 91. Even if a tension higher than an allowable limit acts on the cylinder 94, it is still possible to avoid breakage of the cylinder 94.

In addition, according to this modification, the cylinder 94 is connected to the enclosing portion 91 rotatably along the circumferential direction about the central axis C of the enclosing portion 91. According to this configuration, if a tension is applied on the cylinder 94 to a certain degree or higher in a twisting direction during rotating operation of the enclosing portion 91, the cylinder 94 is allowed to rotate or revolve in the circumferential direction that relieves the tension. It is, therefore, possible to prevent a tension, which acts on the cylinder 94, from impeding rotating operation of the enclosing portion 91. Even if a tension higher than an allowable limit acts on the cylinder 94, it is still possible to avoid breakage of the cylinder 94.

Figure 26:
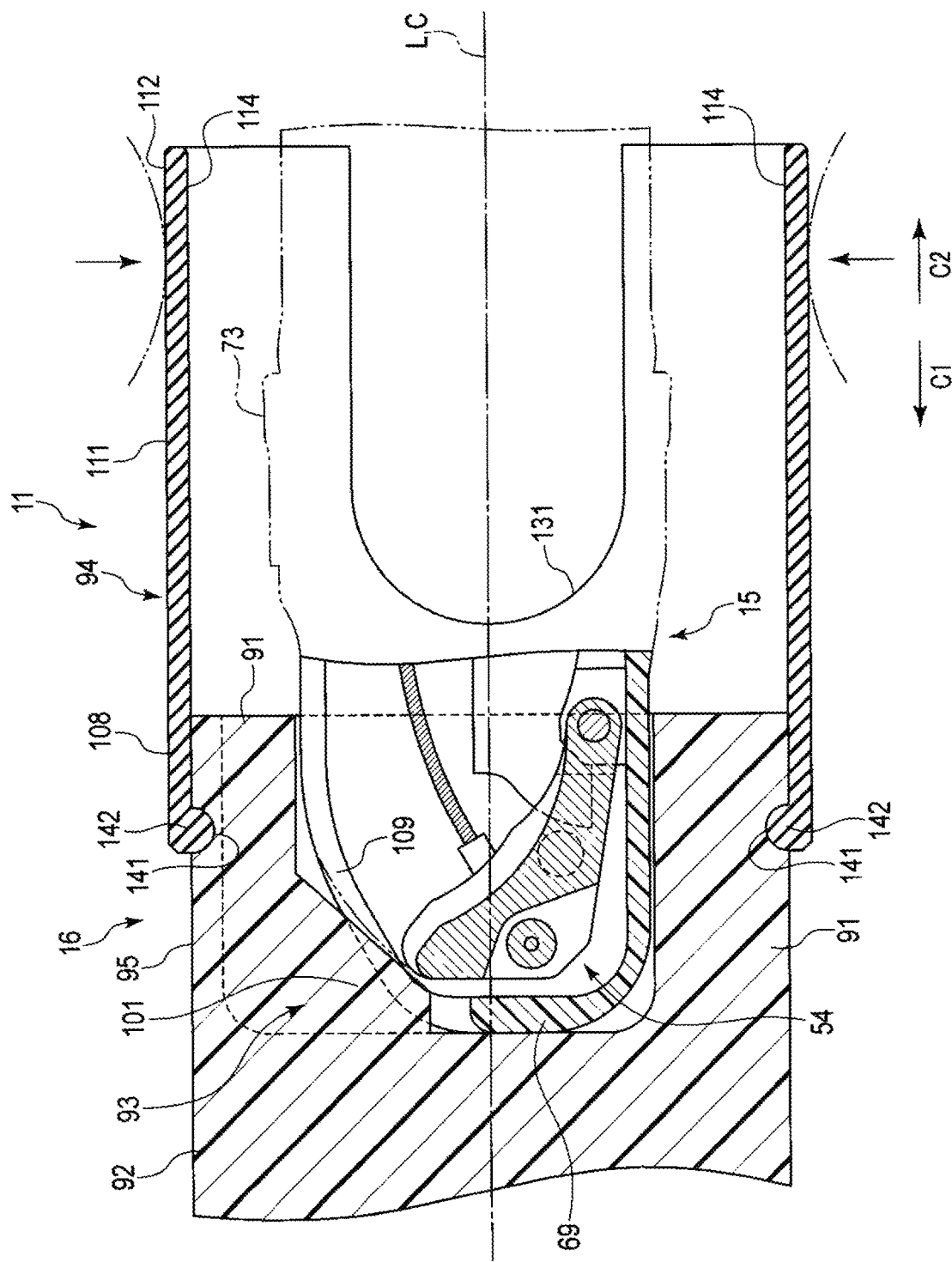
FIG. 26 is a cross-sectional view illustrating a cover removal jig in an eighth modification of the embodiment.

Eighth Modification:

With reference to FIG. 26, a description will be made about an endoscope system 11 according to an eighth modification. The eighth modification is different in the shape of a cylinder 94 from the seventh modification. In this modification, a description will thus be made primarily about those which are different from the corresponding ones in the seventh modification, and an illustration or description will hence be omitted about those which are common to both.

Different from the seventh modification, the cylinder 94 has a diameter equal to that of the enclosing portion 91. Unlike the seventh modification, the cylinder 94 in this modification, therefore, does not have any reduced diameter portion reduced in diameter on a side in the direction C2 toward the proximal end, specifically on a side opposite to the end portion connected to the enclosing portion 91. Accordingly, the cylinder 94 has an inner diameter, which is greater than the diameter of the holding ring 73 of the tip cover 15, the holding ring 73 being the portion where the diameter becomes greatest in the structure including the tip cover 15, wound thread coil 35 and insertion portion 21. A clearance of a certain width is, hence, left between the inner circumferential wall of the cylinder 94 and the outer circumferential wall of the holding ring 73 in a state that the distal end structure part 24 is inserted in the control section 22. Further, the cylinder 94 has a pair of notched portions 131 as in the fourth modification.

According to this modification, basically similar functions as in the case of the cover removal jig 16 of the seventh modification can be exerted. Described specifically, the cylinder 94 in this modification is elastically or flexibly deformable inward under an external force as in the above-described embodiment, and therefore its gripping force for holding the insertion portion 21 is not adversely affected by its large diameter. Further, in this modification, the pair of notched portions 131 as in the fourth modification is provided so that the visibility of an interior of the working portion 93 may be improved compared with the seventh modification.

Figure 27:
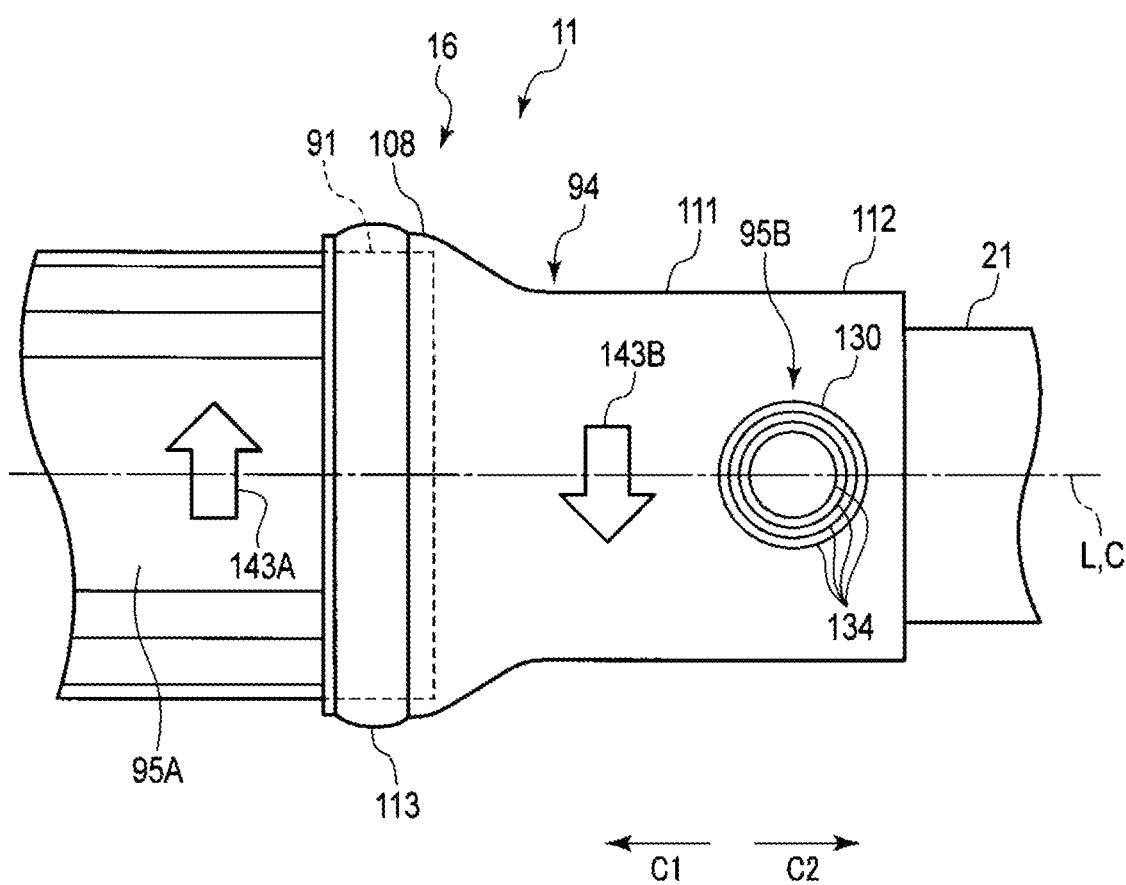
FIG. 27 is a plan view illustrating a cover removal jig and an insertion portion in a ninth modification of the embodiment.

Ninth Modification:

With reference to FIG. 27, a description will be made about an endoscope system 11 according to a ninth modification. In the arrangement of a marker 95B indicating a position where a force is to be applied to the cylinder 94 from the outside, in the arrangement of a second marker 143A, which indicates a rotating direction, on the enclosing portion 91, and in the arrangement of an additional second marker 143B, which indicates another rotating direction, on the cylinder 94, the ninth modification is different from the above-described embodiment.

In this modification, the marker 95A arranged on the grip handle 92 and working portion 93 also includes the second marker 143A formed of an arrow that indicates a rotating direction for the working portion 93. The second marker 143A indicates a direction in which the working portion 93 should be rotated relative to the cylinder 94 and the insertion portion 21 gripped by the cylinder 94. The direction indicated by the second marker 143A is a first direction out of the circumferential directions about the central axis C. The second marker 143A may preferably be formed depressed or protruding from a surrounding part, like a carved mark formed on the planar surface that makes up the marker 95A.

The cylinder 94 has the marker 95B arranged on the reduced diameter portion 111, and the additional second marker 143B arranged adjacent the marker 95B on the reduced diameter portion 111. The marker 95B indicates the position where an operator should apply a force from the outside. The marker 95B is formed of plural grooves 134 formed in an area of substantially the same size as a finger, for example, the thumb of the operator. The plural grooves 134 are formed, for example, in the form of double to quintuple rings so that they surround a central part of the area. The plural grooves 134 each have a circular or oval form. This modification includes the single marker 95B, but two markers 95B may be arranged in pair on both sides with the central axis C interposed therebetween. Further, the marker 95B also functions as a slip resistant element, specifically, the second anti-slip portion 130 that prevents the operator's hand from slipping on the cylinder 94 when the operator grips the cylinder 94.

The additional second marker 143B indicates a direction in which the cylinder 94 and the insertion portion 21 gripped by the cylinder 94 should be rotated relative to the working portion 93. The direction indicated by the additional second marker 143B is a second direction out of the circumferential directions about the central axis C, the second direction being opposite to the first direction. The additional second marker 143B may preferably be formed depressed or protruding from a surrounding part, like a carved mark, on the reduced diameter portion 111.

A description will be made about operation of the cover removal jig 16 in this modification and the endoscope system 11 including the cover removal jig 16.

If the cylinder 94 is disposed in continuation with the enclosing portion 91 as in the above-described embodiment, the visibility of the interior of the working portion 93 is lowered so that an operator may have difficulty in finding in which direction the enclosing portion 91, specifically the working portion 93 should be rotated. According to this modification, it is possible to clearly indicate the rotating direction for the enclosing portion 91 and the rotating direction for the cylinder 94 by the second marker 143A and the additional second marker 143B, and therefore there is no difficulty for the operator in finding these directions.

According to this modification, the cylinder 94 has the additional second marker 143B indicating the direction in which the cylinder 94 should be rotated relative to the enclosing portion 91. On the other hand, the enclosing portion 91 has the second marker 143A indicating the direction in which the enclosing portion 91 should be rotated relative to the cylinder 94. These configurations can facilitate for the operator to find the rotating directions of the enclosing portion 91 and cylinder 94 upon conducting removal operation of the tip cover 15. As a consequence, it is possible to realize a user-friendly cover removal jig 16, with which the user has no difficulty in finding proper rotating directions during removal work, and also an endoscope system 11 including the cover removal jig 16.

In the above-described embodiment and respective modifications, the endoscopes in each of which the distal end structure part 24 is of the side view type are described by way of example. Obviously, these endoscopes may each be formed as a so-called direct view type that allows to observe in a direction along the longitudinal direction L of the insertion portion 21 or as a so-called perspective view type that allows to observe in a desired direction between a direction along the longitudinal direction L of the insertion portion 21 and a direction orthogonal to the longitudinal direction L.

In sum, one aspect of the disclosed technology is directed to a cover removal jig for an endoscope used to remove a first tip cover attached to a distal end of an insertion portion of the endoscope. The cover removal jig comprises a first enclosing portion configured to encapsulate the first tip cover and having a portion engages with the first tip cover. A cylinder is configured to flexibly be connected to the first enclosing portion and capable of coming into close contact with a part of an outer surface of the insertion portion.

The cylinder extends from the first enclosing portion in a direction along a longitudinal direction of the insertion portion. The cylinder includes respective first and second anti-slip portions being formed on respective inner and outer circumferential walls thereof. The first anti-slip portion includes a plurality of concavities and convexities formed on the inner circumferential wall of the cylinder. The second anti-slip portion includes a plurality of grooves formed on the outer circumferential wall of the cylinder. The cover removal jig for an endoscope further comprises a grip handle configured to be attached to the first enclosing portion on a side thereof opposite to a side thereof where the cylinder is connected. The grip handle includes a third anti-slip portion on an outer circumferential wall thereof. The grip handle has an inner diameter greater than an outer diameter of the insertion portion. The cover removal jig for an endoscope further comprises a second enclosing portion configured to be attached to the grip handle on a side thereof opposite from the first enclosing portion. The second enclosing portion is configured to encapsulate a second tip cover having a diameter different from that of the first tip cover, and having a portion being engageable with the second tip cover. The cylinder includes a first marker used to indicate a position where a force should be applied by an operator. The cover removal jig for an endoscope further comprises a second marker is formed on the cylinder to indicate a direction in which the cylinder should be rotated relative to the first enclosing portion. The cover removal jig for an endoscope further comprises a second marker is formed on the first enclosing portion to indicate a direction in which the first enclosing portion is rotated relative to the cylinder. The first enclosing portion and the cylinder are rotatable about a common axis that extends along a central axis of the insertion portion. The cylinder includes a notched portion at a position deviated from a portion where the cylinder is gripped by an operator. The cylinder is detachably connected to the first enclosing portion.

Another aspect of the disclosed technology is an endoscope system comprises a cover removal jig as described hereinbefore and in addition the endoscope system includes an endoscope having the insertion portion to be inserted into a lumen and the first tip cover is attached to the distal end of the insertion portion.

A further aspect of the disclosed technology is directed to a cover removal jig used in an endoscope that comprises an enclosing portion and a cylinder being attached to the enclosing portion to conceal the enclosing portion. The cover removal jig is configured to be engaged with the endoscope to remove a portion of endoscope after being used in a body. The cylinder is elastically attached to the enclosing portion. The cylinder has an inner surface and the inner surface is configured to come into contact with a part of an outer surface of an insertion portion of the endoscope.

The disclosed technology is directed to a cover removal jig kit retrofit to an endoscope system that comprises an endoscope having an insertion portion to be inserted into a lumen. The insertion portion includes a first tip cover attached to a distal end thereof. The cover removal jig being used to remove the first tip cover from the insertion portion of the endoscope. The cover removal jig comprises a first enclosing portion configured to encapsulate the first tip cover and having a portion being engageable with the first tip cover. A cylinder is configured to be flexibly connected to the first enclosing portion capable of coming into a close contact with a part of the insertion portion.

The embodiment and modification has been specifically described with reference to the drawings. However, the disclosed technology should not be restricted to the above-described embodiment and modification, but can be embodied by altering one or more elements within a scope not departing from the spirit thereof. Further, the elements described in the embodiment and the first to ninth modifications can be undoubtedly combined together as needed to realize a single endoscope system 11.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

NUMERAL REFERENCES LIST

11 . . . Endoscope system, 12 . . . Endoscope, 15 . . . Tip cover, 16 . . . Cover removal jig, 21 . . . Insertion portion, 91 . . . Enclosing portion, 92 . . . Grip handle, 94 . . . Cylinder, 95 . . . Marker, 96 . . . Third anti-slip portion, 114 . . . Anti-slip portion, 115 . . . Convex portion, 116 . . . Concave portion, 123 . . . Second tip cover, 125 . . . Second enclosing portion, 130 . . . Second anti-slip portion, 131 . . . Notched portion, 134 . . . Groove, 143A . . . Second marker, 143B . . . Additional second marker.

What is claimed is:

1. A cover removal jig for an endoscope used to remove a first tip cover attached to a distal end of an insertion portion of the endoscope, the cover removal jig comprising:
    a first enclosing portion configured to encapsulate the first tip cover and having a portion being engageable with the first tip cover; and
    a cylinder being flexible and configured to connect to the first enclosing portion and capable of coming into close contact with a part of an outer surface of the insertion portion.

2. The cover removal jig for an endoscope of claim 1, wherein the cylinder extends from the first enclosing portion in a direction along a longitudinal direction of the insertion portion.

3. The cover removal jig for an endoscope of claim 1, wherein the cylinder includes a first anti-slip portion being formed on an inner circumferential wall thereof.

4. The cover removal jig for an endoscope of claim 3, wherein the first anti-slip portion includes a plurality of concavities and convexities formed on the inner circumferential wall of the cylinder.

5. The cover removal jig for an endoscope of claim 1, wherein the cylinder includes a second anti-slip portion on an outer circumferential wall thereof.

6. The cover removal jig for an endoscope of claim 5, wherein the second anti-slip portion includes a plurality of grooves formed on the outer circumferential wall of the cylinder.

7. The cover removal jig for an endoscope of claim 1, further comprising:
    a grip handle configured to be attached to the first enclosing portion on a side thereof opposite to a side thereof where the cylinder is connected.

8. The cover removal jig for an endoscope of claim 7, wherein the grip handle includes a third anti-slip portion on an outer circumferential wall thereof.

9. The cover removal jig for an endoscope of claim 7, wherein the grip handle has an inner diameter greater than an outer diameter of the insertion portion.

10. The cover removal jig for an endoscope of claim 7, further comprising:
    a second enclosing portion configured to be attached to the grip handle on a side thereof opposite from the first enclosing portion and wherein the second enclosing portion is configured to encapsulate a second tip cover having a diameter different from that of the first tip cover, and having a portion being engageable with the second tip cover.

11. The cover removal jig for an endoscope of claim 1, wherein the cylinder includes a first marker used to indicate a position where a force should be applied by an operator.

12. The cover removal jig for an endoscope of claim 1, further comprising: a second marker is formed on the cylinder to indicate a direction in which the cylinder should be rotated relative to the first enclosing portion.

13. The cover removal jig for an endoscope of claim 1, further comprising: a second marker is formed on the first enclosing portion to indicate a direction in which the first enclosing portion is rotated relative to the cylinder.

14. The cover removal jig for an endoscope of claim 1, wherein the first enclosing portion and the cylinder are rotatable about a common axis that extends along a central axis of the insertion portion.

15. The cover removal jig for an endoscope of claim 1, wherein the cylinder includes a notched portion at a position deviated from a portion where the cylinder is gripped by an operator.

16. The cover removal jig for an endoscope of claim 1, wherein the cylinder is detachably connected to the first enclosing portion.

17. The cover removal jig for an endoscope of claim 1, the cylinder further comprising a reduced diameter portion, wherein a diameter of the reduced diameter portion is smaller than a diameter of another portion of the cylinder.

18. The cover removal jig for an endoscope of claim 1, wherein the cylinder includes two semi-cylindrically shaped portions.

19. An endoscope system comprising: the cover removal jig of claim 1; and an endoscope having the insertion portion to be inserted into a lumen and the first tip cover is attached to the distal end of the insertion portion.

20. A cover removal jig for an endoscope comprising:
an enclosing portion; and
a cylinder being attached to the enclosing portion to conceal the enclosing portion, wherein:
the cover removal jig configured to engage with the endoscope to remove a portion of endoscope after being used in a body; and
the cylinder is flexible.

21. The cover removal jig for an endoscope of claim 20, wherein the cylinder is elastically attached to the enclosing portion, and wherein the cylinder has an inner surface and the inner surface is configured to come into contact with a part of an outer surface of an insertion portion of the endoscope.

22. A cover removal jig kit retrofit to an endoscope system comprising:
an endoscope including:
an insertion portion configured to be inserted into a lumen, the insertion portion includes a first tip cover attached to a distal end of the endoscope;
a cover removal jig configured to remove the first tip cover from the insertion portion of the endoscope, the cover removal jig comprising:
a first enclosing portion configured to encapsulate the first tip cover and having a portion being engageable with the first tip cover; and
a cylinder being flexible and configured to connect to the first enclosing portion capable of coming into a close contact with a part of the insertion portion.

* * * * *